(12) United States Patent
Shimada et al.

(10) Patent No.: US 12,161,470 B2
(45) Date of Patent: *Dec. 10, 2024

(54) INTRALUMINAL MICRONEUROGRAPHY DENERVATION PROBE WITH RADIO FREQUENCY ABLATION

(71) Applicant: Otsuka Medical Devices Co., Ltd., Tokyo (JP)

(72) Inventors: Jin Shimada, White Bear Lake, MN (US); Harry A. Puryear, Shoreview, MN (US)

(73) Assignee: Recor Medical, Inc., Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/180,636

(22) Filed: Mar. 8, 2023

(65) Prior Publication Data
US 2023/0218216 A1    Jul. 13, 2023

Related U.S. Application Data

(63) Continuation of application No. 16/517,180, filed on Jul. 19, 2019, now Pat. No. 11,642,061, which is a (Continued)

(51) Int. Cl.
*A61B 5/00* (2006.01)
*A61B 5/20* (2006.01)
(Continued)

(52) U.S. Cl.
CPC ............... *A61B 5/24* (2021.01); *A61B 5/201* (2013.01); *A61B 5/4836* (2013.01); *A61B 5/725* (2013.01);
(Continued)

(58) Field of Classification Search
CPC ....... A61B 5/201; A61B 5/279; A61B 5/6857; A61B 5/6859
See application file for complete search history.

(56) References Cited

U.S. PATENT DOCUMENTS

| 4,643,186 A | 2/1987 | Rosen |
| 4,650,466 A | 3/1987 | Luther |

(Continued)

FOREIGN PATENT DOCUMENTS

| EP | 1299035 | 4/2003 |
| EP | 1503685 | 2/2005 |

(Continued)

OTHER PUBLICATIONS

"U.S. Appl. No. 15/996,978, Response filed Apr. 6, 2020 to Restriction Requirement mailed Feb. 7, 2020", 8 pages.

(Continued)

*Primary Examiner* — Eun Hwa Kim
(74) *Attorney, Agent, or Firm* — Theresa Ann Raymer

(57) ABSTRACT

An intraluminal microneurography probe has a probe body configured to be introduced into an artery near an organ of a body without preventing the flow of blood through the artery. An expandable sense electrode and an expandable stimulation electrode are fixed to the probe body at one end of each electrode such that movement of the other end toward the fixed end causes the sense electrode to expand from the probe body toward a wall of the artery. A ground electrode is configured to couple to the body, and a plurality of electrical connections are operable to electrically couple the electrodes to electrical circuitry. The sense electrode is operable to measure sympathetic nerve activity in response to excitation of the stimulation electrode. A radio frequency ablation element is located between the expandable sense (Continued)

electrode and expandable stimulation electrode, and is operable to ablate nerves proximate to the artery.

20 Claims, 9 Drawing Sheets

Related U.S. Application Data continuation of application No. 15/299,694, filed on Oct. 21, 2016, now abandoned, which is a continuation of application No. 15/204,349, filed on Jul. 7, 2016, now abandoned.

(60) Provisional application No. 62/198,382, filed on Jul. 29, 2015.

(51) Int. Cl.
- *A61B 5/24* (2021.01)
- *A61B 18/14* (2006.01)
- *A61B 18/18* (2006.01)
- *A61N 1/18* (2006.01)
- *A61B 18/00* (2006.01)
- *A61B 18/12* (2006.01)
- *A61B 18/16* (2006.01)

(52) U.S. Cl.
CPC ...... *A61B 18/1492* (2013.01); *A61B 18/1815* (2013.01); *A61N 1/18* (2013.01); *A61B 2018/00023* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00839* (2013.01); *A61B 2018/1253* (2013.01); *A61B 2018/126* (2013.01); *A61B 2018/1407* (2013.01); *A61B 2018/1467* (2013.01); *A61B 2018/162* (2013.01); *A61B 2018/1861* (2013.01); *A61B 2562/028* (2013.01)

(56) References Cited

U.S. PATENT DOCUMENTS

| | | | |
|---|---|---|---|
| 4,709,698 | A | 12/1987 | Johnston et al. |
| 4,841,977 | A | 6/1989 | Griffith et al. |
| 4,983,169 | A | 1/1991 | Furukawa |
| 5,000,185 | A | 3/1991 | Yock |
| 5,114,423 | A | 5/1992 | Kasprzyk |
| 5,368,591 | A | 11/1994 | Lennox |
| 5,391,197 | A | 2/1995 | Burdette et al. |
| 5,423,811 | A | 6/1995 | Imran et al. |
| 5,558,672 | A | 9/1996 | Edwards et al. |
| 5,575,788 | A | 11/1996 | Baker et al. |
| 5,657,755 | A | 8/1997 | Desai |
| 5,685,839 | A | 11/1997 | Edwards et al. |
| 5,688,266 | A | 11/1997 | Edwards et al. |
| 5,800,482 | A | 9/1998 | Pomeranz et al. |
| 6,066,134 | A | 5/2000 | Eggers et al. |
| 6,097,985 | A | 8/2000 | Kasevich et al. |
| 6,117,101 | A | 9/2000 | Diederich et al. |
| 6,254,598 | B1 | 7/2001 | Edwards |
| 6,283,989 | B1 | 9/2001 | Laufer et al. |
| 6,292,695 | B1 | 9/2001 | Webster |
| 6,296,619 | B1 | 10/2001 | Brisken et al. |
| 6,383,151 | B1 | 5/2002 | Diederich et al. |
| 6,514,249 | B1 | 2/2003 | Maguire et al. |
| 6,529,756 | B1 | 3/2003 | Phan |
| 6,584,360 | B2 | 6/2003 | Franschelli et al. |
| 6,635,054 | B2 | 10/2003 | Fjield et al. |
| 6,648,883 | B2 | 11/2003 | Franschelli et al. |
| 6,669,655 | B1 | 12/2003 | Acker |
| 6,692,490 | B1 | 2/2004 | Edwards |
| 6,719,755 | B2 | 4/2004 | Sliwa, Jr. et al. |
| 6,763,722 | B2 | 7/2004 | Field et al. |
| 6,837,886 | B2 * | 1/2005 | Collins ............ A61B 18/1492 606/41 |
| 6,954,977 | B2 | 10/2005 | Maguire |
| 7,052,695 | B2 | 5/2006 | Kalish |
| 7,156,816 | B2 | 1/2007 | Schwartz et al. |
| 7,162,303 | B2 | 1/2007 | Levin et al. |
| 7,371,231 | B2 | 5/2008 | Rioux et al. |
| 7,617,005 | B2 | 11/2009 | Demarais et al. |
| 7,621,873 | B2 | 11/2009 | Owen et al. |
| 7,653,438 | B2 | 1/2010 | Deem et al. |
| 7,717,948 | B2 | 5/2010 | Demarais et al. |
| 7,942,871 | B2 | 5/2011 | Thapliyal et al. |
| 8,024,050 | B2 | 9/2011 | Libbus et al. |
| 8,025,688 | B2 | 9/2011 | Diederich et al. |
| 8,137,274 | B2 | 3/2012 | Weng et al. |
| 8,447,414 | B2 | 5/2013 | Johnson et al. |
| 8,483,831 | B1 | 7/2013 | Hiavka et al. |
| 8,626,300 | B2 | 1/2014 | Demarais et al. |
| 8,702,619 | B2 | 4/2014 | Wang |
| 8,774,913 | B2 | 7/2014 | Demarais et al. |
| 8,790,281 | B2 | 7/2014 | Diederich et al. |
| 8,818,514 | B2 | 8/2014 | Zarins et al. |
| 8,845,629 | B2 | 9/2014 | Demarais et al. |
| 8,932,289 | B2 | 1/2015 | Mayse et al. |
| 9,022,948 | B2 | 5/2015 | Wang |
| 9,028,472 | B2 | 5/2015 | Mathur et al. |
| 9,066,720 | B2 | 6/2015 | Ballakur et al. |
| 9,072,902 | B2 | 7/2015 | Mathur et al. |
| 9,155,590 | B2 | 10/2015 | Mathur |
| 9,186,198 | B2 | 11/2015 | Demarais et al. |
| 9,186,212 | B2 | 11/2015 | Nabulovsky et al. |
| 9,289,132 | B2 | 3/2016 | Ghaffari |
| 9,326,816 | B2 | 5/2016 | Srivastava |
| 9,327,123 | B2 | 5/2016 | Yamasaki |
| 9,333,035 | B2 | 5/2016 | Rudie |
| 9,339,332 | B2 | 5/2016 | Srivastava |
| 9,345,530 | B2 | 5/2016 | Ballakur et al. |
| 9,375,154 | B2 | 6/2016 | Wang |
| 7,717,948 | C1 | 8/2016 | Demarais et al. |
| 9,427,579 | B2 | 8/2016 | Fain et al. |
| 9,439,598 | B2 | 9/2016 | Shimada et al. |
| 9,649,064 | B2 | 5/2017 | Toth et al. |
| 9,723,998 | B2 | 8/2017 | Wang |
| 9,730,639 | B2 | 8/2017 | Toth et al. |
| 9,743,845 | B2 | 8/2017 | Wang |
| 9,750,560 | B2 | 9/2017 | Ballakur et al. |
| 9,770,291 | B2 | 9/2017 | Wang et al. |
| 9,770,593 | B2 | 9/2017 | Gross |
| 9,801,684 | B2 | 10/2017 | Fain |
| 9,820,811 | B2 | 11/2017 | Wang |
| 9,907,983 | B2 | 3/2018 | Thapliyal et al. |
| 9,931,047 | B2 | 4/2018 | Srivastava |
| 9,943,666 | B2 | 4/2018 | Warnking |
| 9,956,034 | B2 | 5/2018 | Toth et al. |
| 9,968,790 | B2 | 5/2018 | Toth et al. |
| 9,981,108 | B2 | 5/2018 | Warnking |
| 9,999,463 | B2 | 6/2018 | Puryear et al. |
| 10,004,458 | B2 | 6/2018 | Toth et al. |
| 10,004,557 | B2 | 6/2018 | Gross et al. |
| 10,010,364 | B2 | 7/2018 | Harringtpm |
| 10,016,233 | B2 | 7/2018 | Pike |
| 10,022,085 | B2 | 7/2018 | Toth et al. |
| 10,039,901 | B2 | 8/2018 | Warnking |
| 10,123,903 | B2 | 11/2018 | Warnking et al. |
| 10,143,419 | B2 | 12/2018 | Toth et al. |
| 10,179,020 | B2 | 1/2019 | Ballakur et al. |
| 10,179,026 | B2 | 1/2019 | Ng |
| 10,182,865 | B2 | 1/2019 | Naga et al. |
| 10,226,633 | B2 | 3/2019 | Toth et al. |
| 10,245,429 | B2 | 4/2019 | Deem et al. |
| 10,292,610 | B2 | 5/2019 | Srivastava |
| 10,293,190 | B2 | 5/2019 | Zarins et al. |
| 10,363,359 | B2 | 7/2019 | Toth et al. |
| 10,368,775 | B2 | 8/2019 | Hettrick et al. |
| 10,376,310 | B2 | 8/2019 | Fain et al. |
| 10,383,685 | B2 | 8/2019 | Gross et al. |
| 10,398,332 | B2 | 9/2019 | Min et al. |

(56) References Cited

U.S. PATENT DOCUMENTS

| | | | |
|---|---|---|---|
| 10,470,684 B2 | 11/2019 | Toth et al. |
| 10,478,249 B2 | 11/2019 | Gross et al. |
| 10,499,937 B2 | 12/2019 | Warnking |
| 10,543,037 B2 | 1/2020 | Shah |
| 10,850,091 B2 | 12/2020 | Zarins et al. |
| 11,801,085 B2 | 10/2023 | Wu et al. |
| 2001/0023365 A1 | 9/2001 | Medhkour et al. |
| 2002/0042610 A1 | 4/2002 | Sliwa, Jr. et al. |
| 2002/0072741 A1 | 6/2002 | Sliwa, Jr. et al. |
| 2002/0165535 A1 | 11/2002 | Lesh |
| 2002/0173724 A1 | 11/2002 | Dorando et al. |
| 2002/0193681 A1 | 12/2002 | Vitek et al. |
| 2003/0004439 A1 | 1/2003 | Pant et al. |
| 2003/0028111 A1 | 2/2003 | Vaezy et al. |
| 2003/0074039 A1 | 4/2003 | Puskas |
| 2003/0125726 A1 | 7/2003 | Maguire et al. |
| 2003/0181963 A1 | 9/2003 | Pellegrino et al. |
| 2003/0216721 A1 | 11/2003 | Diederich et al. |
| 2003/0216792 A1 | 11/2003 | Levin |
| 2004/0019349 A1 | 1/2004 | Fuimaono et al. |
| 2004/0082859 A1 | 4/2004 | Schaer |
| 2004/0097819 A1 | 5/2004 | Duarte |
| 2004/0106880 A1 | 6/2004 | Weng et al. |
| 2004/0122494 A1 | 6/2004 | Eggers et al. |
| 2004/0181178 A1 | 9/2004 | Aldrich et al. |
| 2004/0242999 A1 | 12/2004 | Vitek et al. |
| 2005/0038340 A1 | 2/2005 | Vaezy et al. |
| 2005/0159738 A1 | 7/2005 | Visram et al. |
| 2005/0203501 A1 | 9/2005 | Aldrich et al. |
| 2005/0215990 A1 | 9/2005 | Govari |
| 2005/0228283 A1 | 10/2005 | Gifford et al. |
| 2005/0228459 A1 | 10/2005 | Levin et al. |
| 2005/0228460 A1 | 10/2005 | Levin et al. |
| 2005/0261672 A1 | 11/2005 | Deem et al. |
| 2005/0288730 A1 | 12/2005 | Deem |
| 2006/0041277 A1 | 2/2006 | Deem et al. |
| 2006/0052695 A1 | 3/2006 | Adam et al. |
| 2006/0058711 A1 | 3/2006 | Harhen et al. |
| 2006/0064081 A1 | 3/2006 | Rosinko |
| 2006/0118127 A1 | 6/2006 | Chinn |
| 2006/0142827 A1 | 6/2006 | Willard et al. |
| 2006/0184069 A1 | 8/2006 | Vaitekunas |
| 2006/0217772 A1 | 9/2006 | Libbus et al. |
| 2006/0235286 A1 | 10/2006 | Stone et al. |
| 2007/0060921 A1 | 3/2007 | Janssen et al. |
| 2007/0072741 A1 | 3/2007 | Robideau |
| 2007/0106292 A1 | 5/2007 | Kaplan et al. |
| 2007/0135875 A1 | 6/2007 | Demarais et al. |
| 2007/0265687 A1* | 11/2007 | Deem .............. A61N 1/36139 607/72 |
| 2008/0039746 A1 | 2/2008 | Hissong et al. |
| 2008/0215031 A1 | 9/2008 | Belfort et al. |
| 2009/0234407 A1 | 9/2009 | Hastings et al. |
| 2009/0248005 A1 | 10/2009 | Rusin et al. |
| 2011/0118723 A1 | 5/2011 | Turner et al. |
| 2011/0125206 A1 | 5/2011 | Bornzin |
| 2011/0208096 A1 | 8/2011 | Demarais et al. |
| 2012/0004656 A1 | 1/2012 | Jackson et al. |
| 2012/0265198 A1* | 10/2012 | Crow .............. A61B 18/1492 606/41 |
| 2012/0296232 A1 | 11/2012 | Ng |
| 2012/0296329 A1* | 11/2012 | Ng .............. A61B 18/1492 606/41 |
| 2013/0023897 A1 | 1/2013 | Wallace |
| 2013/0085489 A1 | 4/2013 | Fain et al. |
| 2013/0096550 A1 | 4/2013 | Hill |
| 2013/0116737 A1 | 5/2013 | Edwards et al. |
| 2013/0123770 A1 | 5/2013 | Smith |
| 2013/0131743 A1 | 5/2013 | Yamasaki et al. |
| 2013/0150749 A1 | 6/2013 | McLean et al. |
| 2013/0165925 A1 | 6/2013 | Mathur et al. |
| 2013/0172872 A1 | 7/2013 | Subramaniam |
| 2013/0274614 A1 | 10/2013 | Shimada et al. |
| 2013/0289369 A1 | 10/2013 | Margolis |
| 2013/0289682 A1 | 10/2013 | Barman et al. |
| 2014/0018788 A1 | 1/2014 | Engelman et al. |
| 2014/0058294 A1 | 2/2014 | Gross et al. |
| 2014/0257271 A1 | 9/2014 | Mayse et al. |
| 2014/0274614 A1 | 9/2014 | Min et al. |
| 2014/0275924 A1 | 9/2014 | Min et al. |
| 2014/0288551 A1 | 9/2014 | Bharmi et al. |
| 2014/0288616 A1 | 9/2014 | Rawat et al. |
| 2014/0303617 A1* | 10/2014 | Shimada .............. A61B 18/1492 606/41 |
| 2015/0289931 A1 | 10/2015 | Puryear et al. |
| 2016/0000345 A1 | 1/2016 | Kobayashi et al. |
| 2016/0045121 A1 | 2/2016 | Akingba et al. |
| 2017/0027460 A1 | 2/2017 | Shimada et al. |
| 2017/0035310 A1 | 2/2017 | Shimada et al. |
| 2017/0296264 A1 | 10/2017 | Wang |
| 2018/0022108 A1 | 1/2018 | Mori et al. |
| 2018/0042670 A1 | 2/2018 | Wang et al. |
| 2018/0064359 A1 | 3/2018 | Pranaitis |
| 2018/0078307 A1 | 3/2018 | Wang et al. |
| 2018/0185091 A1 | 7/2018 | Toth et al. |
| 2018/0221087 A1 | 8/2018 | Puryear et al. |
| 2018/0249958 A1 | 9/2018 | Toth et al. |
| 2018/0250054 A1 | 9/2018 | Gross et al. |
| 2018/0280082 A1 | 10/2018 | Puryear et al. |
| 2018/0289320 A1 | 10/2018 | Toth et al. |
| 2018/0310991 A1 | 11/2018 | Pike |
| 2018/0333204 A1 | 11/2018 | Ng |
| 2019/0046111 A1 | 2/2019 | Toth et al. |
| 2019/0046264 A1 | 2/2019 | Toth et al. |
| 2019/0076191 A1 | 3/2019 | Wang |
| 2019/0110704 A1 | 4/2019 | Wang |
| 2019/0134396 A1 | 5/2019 | Toth et al. |
| 2019/0151670 A1 | 5/2019 | Toth et al. |
| 2019/0183560 A1 | 6/2019 | Ballakur et al. |
| 2019/0307361 A1 | 10/2019 | Hettrick et al. |
| 2020/0046248 A1 | 2/2020 | Toth et al. |
| 2020/0077907 A1 | 3/2020 | Shimada et al. |

FOREIGN PATENT DOCUMENTS

| | | |
|---|---|---|
| EP | 1579889 | 9/2005 |
| EP | 2359764 | 8/2011 |
| EP | 2430996 | 3/2012 |
| EP | 2842604 | 3/2015 |
| EP | 2968984 | 1/2016 |
| EP | 2995250 | 3/2016 |
| EP | 3799931 | 4/2021 |
| WO | WO1999/002096 | 1/1999 |
| WO | WO2001/095820 | 12/2001 |
| WO | WO2002/005897 | 1/2002 |
| WO | WO 2002/019934 | 3/2002 |
| WO | WO2003/022167 | 3/2003 |
| WO | WO2003/051450 | 6/2003 |
| WO | WO2006/041881 | 4/2006 |
| WO | WO2006/060053 | 6/2006 |
| WO | WO2007/014003 | 2/2007 |

OTHER PUBLICATIONS

"U.S. Appl. No. 15/996,978, Restriction Requirement mailed Apr. 16, 2020", 8 pages.

"U.S. Appl. No. 15/943,354, Non Final Office Action mailed Apr. 20, 2020", 7 pages.

"U.S. Appl. No. 15/996,978, Response filed May 1, 2020 to Restriction Requirement mailed Apr. 16, 2020", 8 pages.

"U.S. Appl. No. 15/996,978, Non Final Office Action mailed Jun. 11, 2020", 8 pages.

"U.S. Appl. No. 15/943,354, Restriction Requirement mailed Nov. 20, 2019", 8 pages.

"U.S. Appl. No. 15/943,354, Response filed Dec. 19, 2019 to Restriction Requirement mailed Nov. 20, 2019", 8 pages.

"U.S. Appl. No. 15/943,354, Non Final Office Action mailed Jan. 13, 2020", 6 pages.

"U.S. Appl. No. 15/996,978, Restriction Requirement mailed Feb. 7, 2020", 7 pages.

"U.S. Appl. No. 14/683,966, 312 Amendment filed Mar. 13, 2018", 10 pgs.

(56) References Cited

OTHER PUBLICATIONS

"U.S. Appl. No. 14/683,966, Corrected Notice of Allowance mailed May 22, 2018", 4 pgs.
"U.S. Appl. No. 14/683,966, Non Final Office Action mailed Jun. 12, 2017", 14 pgs.
"U.S. Appl. No. 14/683,966, Notice of Allowance mailed Jan. 31, 2018", 8 pgs.
"U.S. Appl. No. 14/683,966, PTO Response to Rule 312 Communication mailed Mar. 29, 2018", 2 pgs.
"U.S. Appl. No. 14/683,966, Response filed Nov. 10, 2017 to Non Final Office Action mailed Jun. 12, 2017", 13 pgs.
"U.S. Appl. No. 15/204,349, Advisory Action mailed Jul. 9, 2019", 5 pgs.
"U.S. Appl. No. 15/204,349, Final Office Action mailed Apr. 22, 2019", 16 pgs.
"U.S. Appl. No. 15/204,349, Non Final Office Action mailed Nov. 28, 2018", 14 pgs.
"U.S. Appl. No. 15/204,349, Preliminary Amendment filed Nov. 30, 2016 ", 3 pgs.
"U.S. Appl. No. 15/204,349, Response filed Feb. 27, 2019 to Non Final Office Action mailed Nov. 27, 2018", 10 pgs.
"U.S. Appl. No. 15/204,349, Response filed Jun. 5, 2018 to Restriction Requirement mailed May 17, 2018", 7 pgs.
"U.S. Appl. No. 15/204,349, Response filed Jun. 24, 2019 to Final Office Action mailed Apr. 22, 2019", 12 pgs.
"U.S. Appl. No. 15/204,349, Restriction Requirement mailed May 17, 2018", 7 pgs.
"U.S. Appl. No. 15/299,694, Advisory Action mailed Jul. 9, 2019", 5 pgs.
"U.S. Appl. No. 15/299,694, Final Office Action mailed Apr. 22, 2019", 16 pgs.
"U.S. Appl. No. 15/299,694, Non Final Office Action mailed Nov. 27, 2018", 15 pgs.
"U.S. Appl. No. 15/299,694, Response filed Feb. 27, 2019 to Non-Final Office Action mailed Nov. 27, 2018", 10 pgs.
"U.S. Appl. No. 15/299,694, Response filed Jun. 24, 2019 to Final Office Action mailed Apr. 22, 2019", 11 pgs.
"U.S. Appl. No. 15/299,694, Response filed Oct. 8, 2018 to Restriction Requirement mailed Aug. 6, 2018", 7 pgs.
"U.S. Appl. No. 15/299,694, Restriction Requirement mailed Aug. 6, 2018", 6 pgs.
"U.S. Appl. No. 15/943,354, Preliminary Amendment filed Apr. 3, 2018", 9 pgs.
"U.S. Appl. No. 15/996,978, Preliminary Amendment filed Jun. 5, 2018", 11 pgs.
Accornero, Neri, et al., "Selective Activation of Peripheral Nerve Fibre Groups of Different Diameter By Triangular Shaped Stimulus Pulses", J. Physiol. (1977), 273, OD. 539-560, 22 pgs.
Papademetriou, et al. , "Renal Sympathetic Denervation : Hibernation or Resurrection?", Cardiology 2016; 135, 11 pgs.
U.S. Appl. No. 17/453,636, filed Nov. 4, 2021.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 758-765 (2012).
American Heart Association—Pulmonary Hypertension: High Blood Pressure in the Heart-to-Lung System, (last reviewed Oct. 31, 2016).
Appeal Brief of Patent Owner from Reexamination 95-002, 110.
Aytac, et al., "Correlation Between the Diameter of the Main Renal Artery and the Presence of an Accessory Renal Artery", J Ultrasound Med 22:433-439, 2003 (.
Azizi, Michel et al., Ultrasound renal denervation for hypertension resistant to a triple medication pill (Radiance-HTN Trio): a randomised, multicentre, single-blind, sham-controlled trial, 397 Lancet 2476 (2021).
Bailey, M.R. et al., Physical Mechanisms of the Therapeutic Effect of Ultrasound (A Review), Acoustical Physics, vol. 49, No. 4, 2003, pp. 369-388.

Bengel, et al., Serial Assessment of Sympathetic Reinnervation After Orthotopic Heart Transplantation; A Longitudinal Study Using PET and C-11 Hydroxyephedrine, Circulation. 1999;99:1866-1871.
Berjano, E. et al., "A Cooled Intraesophageal Balloom to Prevent Thermal Injury during Endocardial Surgical Radiofrequency Ablation of the left Atrium: a finite element study." Physics in Medicine and Biology, 50(20): 269-279, 2015.
Bhatt, D.L., et al., A Controlled Trial of Renal Denervation for Resistant Hypertension, New England J. Med., 370:1393-1401 (2014).
Bhatt, Deepak L. et al., Long-term outcomes after catheter-based renal artery denervation for resistant hypertension: final follow-up of the randomised Symplicity HTN-3 Trial, 400 Lancet 1405 (2022).
Billard, B.E. et al., Effects of Physical Parameters on High Temperature Ultrasound Hyperthermia, Ultrasound in Med. & Biol. vol. 16, No. 4, pp. 409-420, 1990.
Bisdas, Theodosios et al., Initial Experience with the 6-F and 8-F Indigo Thrombectomy System for Acute Renovisceral Occlusive Events, Journal of Endovascular Therapy, vol. 24, No. 4, 604-610 (2017).
Blanketjin, Peter, Sympathetic Hyperactivity in Chronic Kidney Disease, Neprhrol Dial Transplant, vol. 19, No. 6, 1354-1357 (2004).
Blum et al., Treatment of Ostial Renal-Artery Stenoses with Vascular Endoprostheses after Unsuccessful Balloon Angioplasty, N. Engl. J. Med. 336 459-65 (1997).
Bonsignore, C., "A Decade of Evolution in Stent Design", Proceedings of the International Conference on Shape Memory and Superelastic Technologies, (2003).
Bradfield, Jason S. et al., Renal denervation as adjunctive therapy to cardiac sympathetic denervation for ablation refractory ventricular tachycardia, Heart Rhythm Society, vol. 17, No. 2, 220-227 (2020).
Bush, et al., "Endovascular revascularization of renal artery stenosis: Technical and clinical results", Journal of Vascular Surgery, 2001, May, 1041-1049 (2001).
Camasao, D. B. et al., The mechanical characterization of blood vessels and their substitutes in the continuous quest for physiological-relevant performances: A critical review, Materials Today Bio, vol. 10 (2021).
Carter, J., "Microneurography and Sympathetic Nerve Activity: A Decade-By-Decade Journey across 50 Years," Journal of Neurophysiology, vol. 121, No. 4. doi: 10.1 152/jn.00570.2018.
Carter, Stefan et al., Measurement of Renal Artery Pressures by Catheterization in Patients with and without Renal Artery Stenosis, Circulation, vol. XXXIII, 443-449 (1966).
Chapelon, J.Y., "Treatment of Localised Prostate Cancer with Transrectal High Intensity Focused Ultrasound," European Journal of Ultrasound 9, 31-38, 1999.
Charlesworth, Peter et al., Renal Artery Injury from a Fogarty Balloon Catheter, Journal of Vascular Surgery, vol. 1, No. 4, 573-576 (1984).
Chart showing priority claims of the '629 patent, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Chiesa et al., Endovascular Stenting for the Nutcracker Phenomenon, J. Endovasc. Ther., 8:652-655 (2001).
Coates, Paul et al., "Time, Temperature, Power, and Impedance Considerations for Radiofrequency Catheter Renal Denervation," Cardiovascular Revascularization Medicine 42, 171-177 (2022).
Corrected Patent Owner's Response to Office Action, dated May 10, 2013, from File History of Inter Partes Reexamination U.S. Appl. No. 95/002,110.
Correspondence from PTAB Deputy Chief Clerk to Counsel re conference call request—Exhibit 3001 in the Patent Trial and Appeal Board, United States Patent and Trademark Office, Petition No. PTAB-IPR2022-00431.
Curriculum Vitae of Dr. Chris Daft.
Curriculum Vitae of Dr. John M. Moriarty.
Curriculum Vitae of Dr. Michael Bohm.
Curriculum Vitae of Farrell Mendelsohn.

(56) References Cited

OTHER PUBLICATIONS

Dangas, G., et al., Intravascular Ultrasound-Guided Renal Artery Stenting, J Endovasc Ther, 2001;8:238-247 (2001).
Deardorff, Dana et al., Ultrasound Applicators with Internal Water-Cooling for High-Powered Interstitial Thermal Therapy, IEEE Transactions on Biomedical Engineering, vol. 47, No. 10, 1356-1365 (2000).
Deardorff, Dana et al., Ultrasound Applicators with Internal Cooling for Interstitial Thermal Therapy, SPIE vol. 3594, 36-46, Jan. 1999.
Decision of the Patent Trial and Appeal Board in U.S. Appl. No. 14/731,347.
Declaration of Chris Daft dated Jan. 11, 2022, in the Patent Trial and Appeal Board, United States Patent and Trademark Office, Petition No. PTAB-IPR2022-00431.
Second Declaration of Chris Daft. Dated Jan. 10, 2023, in the Patent Trial and Appeal Board, United States Patent and Trademark Office, Petition No. PTAB-IPR2022-00431.
Declaration of Dr. Daniel van der Weide, dated Oct. 26, 2022, in the Patent Trial and Appeal Board, United States Patent and Trademark Office, Petition No. PTAB-IPR2022-00431.
Declaration of Dr. Dieter Haemmerich, dated Aug. 29, 2012, in the Patent Trial and Appeal Board, United States Patent and Trademark Office, In re U.S. Pat. No. 7,717,948.
Declaration of Dr. John M. Moriarty in German Nullity proceedings for EP2261905 dated Jul. 13, 2022.
Declaration of Dr. John Moriarty, dated Jan. 19, 2023, in the Patent Trial and Appeal Board, United States Patent and Trademark Office, Petition No. PTAB-IPR2022-00431.
Declaration of Jonathan Bradford in Support of Patent Owner's Response, dated Oct. 27, 2022.
Declaration of Jonathan Bradford dated May 10, 2022, in the Patent Trial and Appeal Board, United States Patent and Trademark Office, Petition No. PTAB-IPR2022-00431.
Declaration of Dr. Michael Bohm dated Sep. 29, 2022 on behalf of Medtronic Inc.
Declaration of Dr. Robert Tucker, dated Oct. 27, 2022, in the Patent Trial and Appeal Board, United States Patent and Trademark Office, Petition No. PTAB-IPR2022-00431.
Declaration of Farrell Mendelsohn dated Jan. 10, 2022, in the Patent Trial and Appeal Board, United States Patent and Trademark Office, Petition No. PTAB-IPR2022-00431.
Defendant's Reply to Court Order of Oct. 4, 2022 and Plaintiff's Surrejoinder of Sep. 29, 2022 in the Mannheim District Court, case No. 7 O 14/21, dated Oct. 31, 2022.
Defendant's Response dated May 11, 2022 in the Munich Federal Patent Court, Nullity Suit 6 Ni 32/22.
Dibona, Gerald F., "Neural Control of the Kidney, Past, Present and Future," 41 [Part II] Hypertension 621 24 (2003).
Dibona, Gerald, Sympathetic Nervous System and Kidney in Hypertension, Current Opinion in Nephrology and Hypertension, vol. 11, 197-200 (2002).
Dibona, Gerald F et al., "Neural Control of Renal Function", 77 Physiological Reviews No. 1, 75 (1997).
Diederich, et al., "Catheter-based Ultrasound Applicators for Selective Thermal Ablation: progress towards MRI-guided applications in prostate," International Journal of Hyperthermia, 20:7, 739-756.
Diederich, et al., "Transurethral Ultrasound Applicators with Directional Heating Patterns for Prostate Thermal Therapy: In vivo evaluation using magnetic resonance thermometry," Med. Phys. 31 (2), 405-413, Feb. 2004.
Diederich, et al., Ultrasound Catheters for Circumferential Cardiac Ablation, in Proceedings of SPIE Conference on Thermal Treatment of Tissue with Image Guidance San Jose, California, Jan. 1999 SPIE vol. 3594.
Diedrich, A. et al.,"Analysis of Raw Microneurographic Recordings Based on Wavelet De-Noising Technique and 1 Classification Algorithm: Wavelet Analysis in Microneurography," IEEE Trans Biomed Eng. Jan. 2003; 50(1): 41-50_ doi:10.1109fTBME.2002.807323.
Draney, Mary et al., Three-Dimensional Analysis of Renal Artery Bending Motion During Respiration, International Society of Endovascular Specialists, vol. 12, 380-386 (2005).
Erikson, Kenneth et al., Ultrasound in Medicine: A Review, IEEE Transactions on Sonics and Ultrasonics, vol. 21, No. 3 (1974).
EP Board of Appeals Communication dated Dec. 17, 2019—Preliminary Remarks for EP appeal No. T2680/16-3.3.4.01.
European Search Report in Application No. 12180431.4 dated Jan. 17, 2013.
European Communication in Application No. 12180431.4 dated Oct. 23, 2013.
European Office Action in Application No. 12180431.4.
European Patent No. 12167931, Claims of the Main Request dated Sep. 30, 2016.
European Search Report (Supplementary) in Application No. 14775754.6 dated Feb. 17, 2016.
European Search Report in Application No. 218186547 dated Nov. 19, 2018.
European Search Report in Application No. 20202272.9 dated Mar. 1, 2021.
Fan, Xiaobing et al., "Control of the Necrosed Tissue Volume during Noninvasive Ultrasound Surgery using a 16-Element Phased Array," Department of Radiology, Brigham and Women's Hospital, Harvard Medical School, Oct. 31, 1994.
Fengler, Karl et al., A Three-Arm Randomized Trial of Different Renal Denervation Devices and Techniques in Patients with Resistant Hypertension (Radiosound-HTN), 139 Circulation 590 (2019).
File History to EP1802370B1 Part 1.
File History to EP1802370B1 Part 2.
File History to EP1802370B1 Part 3.
Foley, Jessica L., et al., "Image-Guided HIFU Neurolysis of Peripheral Nerves to Treat Spasticity and Pain," Ultrasound in Med & Biol., vol. 30, Np. 9 pp. 1199-1207, 2004.
Gallitto, Enrico et al., Renal Artery Orientation Influences the Renal Outcome in Endovascular Thoraco-abdominal Aortic Aneurysm Repair, European Society of Endovascular Surgery, vol. 56, No. 3, 382-390 (2018).
Gervais, Debra A. et al., Radiofrequency ablation of renal cell carcinoma: Part 2, Lessons learned with ablation of 100 tumors, 185 AJR Am. J. Roentgenol. 72 (2005).
Goldberg, S. Nahum et al., EUS-guided radiofrequency ablation in the pancreas: results in a porcine model, 50 Gastrointest. Endosc. 392 (1999).
Golwyn et al., Percutaneous Transcatheter Renal Ablation with Absolute Ethanol for Uncontrolled Hypertension or Nephrotic Syndrome: Results in 11 Patients with End-Stage Renal Disease, J. Vasco and Interventional Radiology, 8,527-433 (1997).
Gorsich, W., et al., Heat-Induced Contraction of Blood Vessels, Lasers in Surgery and Medicine, 2:1-13 (1982).
Gray, Henry, Gray's Anatomy: The Anatomical Basis of Medicine and Surgery, Churchill Livingstone, New York, NY (1995).
Habict, Antje et al., Sympathetic Overactivity and Kidneys, The Middle European Journal of Medicine, vol. 115, 634-640 (2003).
Hansen et al., The Transplanted Human Kidney Does Not Achieve Functional Reinnervation, 87 Clinical Science 13 (1994).
Harrison, R. R. et al., "A Low-Power Integrated Circuit for a Wireless 1 OD-Electrode Neural Recording System," IEEE Journal of Solid-State Circuits, vol. 42, No. 1, pp. 123-133, Jan. 2007. doi: 10.1 109/JSSC.2006.886567.
He, D. S. et al., Application of Ultrasound Energy for Intracardiac Ablation of Arrhythmias, European Heart Journal, vol. 16, 961-966 (1995).
Heffner, H. et al., "Gain, Band Width, and Noise Characteristics of the Variable-Parameter Amplifier," Journal of Applied Physics, vol. 29, No. 9, Sep. 1958, 1 1 pages.
Holmes, David R. et al., Pulmonary vein stenosis complicating ablation for atrial fibrillation: clinical spectrum and interventional considerations, 2 JACC Cardiovasc. Interv. 267 (2009).
Hsu, Thomas H. S. et al., Radiofrequency ablation of the kidney: acute and chronic histology in porcine model, 56 Urology 872 (2000).

(56) References Cited

OTHER PUBLICATIONS

Huang, S.K.S. and Wilbur, D. Eds, Radiofrequency Catheter Ablation of Cardiac Arrhythmias, Basic Concepts and Clinical Applications, Futura Publishing Company, Inc., Armonk, New York (2000).
Huang, et al., Renal Denervation Prevents and Reverses Hyperinsulinemia-Induced Hypertension in Rats, Hypertension 32 (1998) pp. 249-254.
Institution Decision Granting Institution of Inter Partes Review 35 U.S.C. sec. 314, dated Aug. 8, 2022 in the Patent Trial and Appeal Board, United States Patent and Trademark Office, Petition No. PTAB-IPR2022-00431.
Isles et al., Management of Renovascular Disease: A Review of Renal Artery Stenting in Ten Studies, QJM 92, 159-67 (1999).
Ivanisevic, N., "Circuit Design Techniques for Implantable Closed-Loop Neural Interfaces," Doctoral Thesis in Information and Communication Technology, KTH School of Electrical Engineering and Computer Science, Sweden, May 2019, 92 pages.
Janssen, B. J. A., et al. "Renal nerves in hypertension." Miner Electrolyte Metab., 15:74-82 (1989).
Janzen, Nicolette et al., Minimally Invasive Ablative Approaches in the Treatment of Renal Cell Carcinoma, Current Urology Reports, vol. 3 (2002).
Kaltenbach, Benjamin et al., Renal Artery Stenosis After Renal Sympathetic Denervation, Journal of the American College of Cardiology, vol. 60, No. 25 (2012).
Kapural, Leonardo, et al., "Radiofrequency Ablation for Chronic Pain Control," Anesthetic Techniques in Pain Management, pp. 517-525, 2001.
Katholi, R.E., et al., Importance of Renal Sympathetic Tone in the Development of DOCA-Salt Hypertension in The Rat, Hypertension, 2:266-273 (1980).
Kim, Yun-Hyeon et al., Pulmonary vein diameter, cross-sectional area, and shape: CT analysis, Radiology Society of North America, vol. 235, No. 1, 49-50 (2005).
Kirsh, Danielle, Balloon Catheters: What are some key design considerations?, Massdevice (Dec. 6, 2016).
Kompanowska-Jezierska, Elzbieta et al., Early Effects of Renal Denervation in the Anaesthetized Rat: Natriuresis and Increased Cortical Blood Flow, 531 J. Physiology No. 2, 527 (2001).
Koomans, Hein et al., Sympathetic Hyperactivity in Chronic Renal Failure: A wake-up call, Frontiers in Nephrology, vol. 15, 524-537 (2004).
Kuo, et al., "Atrial Fibrillation: New Horizons", Chang Gung Med J vol. 26 No. Oct. 10, 2003.
Lang, Roberto et al., Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology, Journal of the American Society of Echocardiography, vol. 18, No. 12, 1440-1463 (2005).
Lee, Jong Deok et al., MR imaging-histopathologic correlation of radiofrequency thermal ablation lesion in a rabbit liver model: observation during acute and chronic stages, 2 Korean J. Radiol. 151 (2001).
Levin, S., et al., Ardian: Succeeding Where Drugs Fail—Treating Hypertension in the Cath Lab, In Vivo, 27:23 (2009).
Mahfoud, Felix et al., Catheter-Based Renal Denervation Is No Simple Matter: Lessons to Be Learned From Our Anatomy?, Journal of the American College of Cardiology, vol. 64, No. 7, 644-647 (2014).
Marine, Joseph E., Catheter ablation therapy for supraventricular arrhythmias, 298 JAMA 2768 (2007).
Martin, Louis G et al., Long-term Results of Angioplasty in 110 Patients with Renal Artery Stenosis, Journal of Vascular and Interventional Radiology, vol. 3, No. 4, 619-626 (1992).
Maslov, P., "Recruitment Pattern of Muscle Sympathetic Nerve Activity in Chronic Stable Heart Failure Patients and in Healthy Control Subjects," Doctoral Dissertation, University of Split, Croatia, 2013, 69 pages.

Matsumoto, Edward D et al., Short-term efficacy of temperature-based radiofrequency ablation of small renal tumors, 65 Urology 877 (2005).
Medtronic Press Release, Medtronic Announces U.S. Renal Denervation Pivotal Trial Fails to Meet Primary Efficacy Endpoint While Meeting Primary Safety Endpoint (Jan. 9, 2014).
Medtronic Inc., Renal Denervation (RDN): Novel Catheter-Based Treatment for Hypertension, Scientific Background, 2011.
Medtronic Scientific Background, Hypertension and the Symplicity Renal Denervation System.
Medtronic, Symplicity RDN Common System Q&A.
Medtronic Inc., The Symplicity RDN System, 2012.
Meyers, Philip et al., Temporary Endovascular Balloon Occlusion of the Internal Carotid Artery with a Nondetachable Silicone Balloon Catheter: Analysis Technique and Cost, American Journal of Neuroradiology, vol. 20, No. 4, 559-564 (1999).
Millard, et al., Renal Embolization for Ablation of Function In Renal Failure And Hypertension, Postgraduate Med. J. 65, 729-734 (1989).
Mitchell, et al., "The Renal Nerves" British Journal of Urology, Read by invitation at the Sixth Annual Meeting of the British Association of Urological Surgeons on Jun. 30, 1950.
Morrissey, D. M. "Sympathectomy in the treatment of hypertension." Lancet, CCLXIV:403-408 (1953).
Nair et al., "The Need for and the Challenges of Measuring Renal Sympathetic Nerve Activity," Heart Rhythm 2016; 13:1166-1171.
Natale, Andrea et al., First Human Experience with Pulmonary Vein Isolation Using a Through-the-Balloon Circumferential Ultrasound Ablation System for Recurrent Atrial Fibrillation, Circulation, vol. 102, 1879-1882 (2000).
Netter, Frank, Atlas of Human Anatomy, Icon Learning Systems, Rochester, NY (2002).
Neumann, Jutta, Sympathetic hyperactivity in chronic kidney disease: Pathogenesis, clinical relevance, and treatment, International Society of Nephrology, vol. 65, 1568-1576 (2004).
News, Columbia University Irving Medical Center, Zapping Nerves with Ultrasound Lowers Drug-Resistant Blood Pressure (May 16, 2021), https://www.cuimc.columbia.edu/news/zapping-nervesultrasound-lowers-drug-resistant-blood-pressure.
Notice of Deposition of Tucker, filed Dec. 30, 2022 in the Patent Trial and Appeal Board, United States Patent and Trademark Office, Petition No. PTAB-IPR2022-00431.
Notice of Deposition of van der Weide, filed Dec. 30, 2022 in the Patent Trial and Appeal Board, United States Patent and Trademark Office, Petition No. PTAB-IPR2022-00431.
Notice re filing date accorded, dated Feb. 10, 2022 in the Patent Trial and Appeal Board, United States Patent and Trademark Office, Petition No. PTAB-IPR2022-00431.
Nozawa, T., et al. "Effects of long-term renal sympathetic denervation on heart failure after myocardial infarction in rats." Heart Vessels, 16:51-56 (2002).
Oliveira, Vera L. et al., "Renal Denervation Normalizes Pressure and Baroreceptor Reflex in High Renin Hypertension in Conscious Rats", 19 Hypertension Suppl. II No. 2, 17 (1992) ("Oliveira 1992").
Olsson, R. et al., "A Three-Dimensional Neural Recording Microsystem with Implantable Data Compression 5 Circuitry," ISSCC. 2005 IEEE International Digest of Technical Papers. Solid-State Circuits Conference, 2005., San Francisco, CA, 2005, pp. 558-559 vol. 1 doi:10.1109/JSSC.2005.858479.
Order: Conduct of the Proceeding Scheduling Order 37 C.F.R. sec. 42.5, dated Aug. 8, 2022 in the Patent Trial and Appeal Board, United States Patent and Trademark Office, Petition No. PTAB-IPR2022-00431.
Order Setting Oral Hearing 37 C.F.R. § 42.70, dated Mar. 24, 2023 in the Patent Trial and Appeal Board, United States Patent and Trademark Office, Petition No. PTAB-IPR2022-00431.
Osborn, J., "Catheter-Based Renal Nerve Ablation as a Novel Hypertension Therapy, Lost, and Then Found," in Translation.
Page, Irvine H. & George J. Heuer, The Effect of Renal Denervation on the Level of Arterial Blood Pressure and Renal Function in Essential Hypertension, 14 J. Clinical Investigation 27 (1935) (received for publication in 1934).

(56) References Cited

OTHER PUBLICATIONS

Page, Irvine H. & George J. Heuer, The Effect of Renal Denervation on Patients Suffering from Nephritis, 14 J. Clinical Investigation 443 (1935) (received for publication in 1935).
Papademetriou, Vasilios et al., Renal Sympathetic Denervation for the Treatment of Difficult-to-Control or Resistant Hypertension, 2011 Int. J. Hypertension, Article 196518 (2011).
Papadopoulos, N., "Evaluation of a Small Flat Rectangular Therapeutic Ultrasonic Transducer Intended for Intravascular Use," Ultrasonics 74, 196-203, 2017.
Pappone C, et al., "Circumferential radiofrequency ablation of pulmonary vein ostia: a new anatomic approach for curing atrial fibrillation", Circulation. 2000; 102(21):2619-2628. (2000).
Patent Owner's Amended Objections to Evidence Under 37 C.F.R. §42.64.
Patent Owner's Mandatory Notice, filed Feb. 3, 2022 in the Patent Trial and Appeal Board, United States Patent and Trademark Office, Petition No. PTAB-IPR2022-00431.
Patent Owner's Notice of Deposition of Dr. Chris Daft, filed Sep. 20, 2022 in the Patent Trial and Appeal Board, United States Patent and Trademark Office, Petition No. PTAB-IPR2022-00431.
Patent Owner's Notice of Deposition of Dr. Chris Daft filed Feb. 21, 2023 in the Patent Trial and Appeal Board, United States Patent and Trademark Office, Petition No. PTAB-IPR2022-00431.
Patent Owner's Notice of Deposition of Dr. Farrell Mendelsohn, filed Sep. 21, 2022 in the Patent Trial and Appeal Board, United States Patent and Trademark Office, Petition No. PTAB-IPR2022-00431.
Patent Owner's Notice of Deposition of Dr. John Moriarty, filed Feb. 21, 2023 in the Patent Trial and Appeal Board, United States Patent and Trademark Office, Petition No. PTAB-IPR2022-00431.
Patent Owner's Objections to Evidence, filed Aug. 18, 2022 in the Patent Trial and Appeal Board, United States Patent and Trademark Office, Petition No. PTAB-IPR2022-00431.
Patent Owner's Power of Attorney, filed Feb. 3, 2022 in the Patent Trial and Appeal Board, United States Patent and Trademark Office, Petition No. PTAB-IPR2022-00431.
Patent Owner Medtronic Ireland Power of Attorney, filed May 10, 2022 in the Patent Trial and Appeal Board, United States Patent and Trademark Office, Petition No. PTAB-IPR2022-00431.
Patent Owner's Preliminary Response, filed May 10, 2022 in the Patent Trial and Appeal Board, United States Patent and Trademark Office, Petition No. PTAB-IPR2022-00431.
Patent Owner's Request for Oral Hearing, filed Mar. 23, 2023 in the Patent Trial and Appeal Board, United States Patent and Trademark Office, Petition No. PTAB-IPR2022-00431.
Patent Owner's Response, filed Oct. 27, 2022 in the Patent Trial and Appeal Board, United States Patent and Trademark Office, Petition No. PTAB-IPR2022-00431.
Patent Owner's Sur-Reply, filed Mar. 9, 2023 in the Patent Trial and Appeal Board, United States Patent and Trademark Office, Petition No. PTAB-IPR2022-00431.
Patent Owner's Updated Mandatory Notice, filed May 10, 2022 in the Patent Trial and Appeal Board, United States Patent and Trademark Office, Petition No. PTAB-IPR2022-00431.
Peet, M.M., Hypertension and Its Surgical Treatment by Bilateral Supradiaphragmatic Splanchnicectomy, Am. J. Surgery, LXXV:48-68 (1948).
Petition for Inter Partes Review of U.S. Pat. No. 8,845,629, dated Jan. 13, 2022 by ReCor Medical, Inc. and Otsuka Medical Devices Co., Ltd., in the Patent Trial and Appeal Board, United States Patent and Trademark Office, Petition No. PTAB-IPR2022-00431.
Petitioner ReCor's Biography of Dr. Neil C. Barman.
Petitioner's Power of Attorney for Otsuka Medical Devices Co., Ltd., filed Jan. 13, 2022 in the Patent Trial and Appeal Board, United States Patent and Trademark Office, Petition No. PTAB-IPR2022-00431.
Petitioner's Power of Attorney for Recor Medical, Inc., filed Jan. 13, 2022 in the Patent Trial and Appeal Board, United States Patent and Trademark Office, Petition No. PTAB-IPR2022-00431.
Petitioner Reply, filed Jan. 23, 2023 in the Patent Trial and Appeal Board, United States Patent and Trademark Office, Petition No. PTAB-IPR2022-00431.
Petitioners' Request for Oral Argument, filed Mar. 21, 2023 in the Patent Trial and Appeal Board, United States Patent and Trademark Office, Petition No. PTAB-IPR2022-00431.
Petitioners' Updated Mandatory Notices, dated Jan. 18, 2022 in the Patent Trial and Appeal Board, United States Patent and Trademark Office, Petition No. PTAB-IPR2022-00431.
Plaintiff's Nullity Brief, dated Jan. 14, 2022, in the Munich Federal Patent Court, Nullity Suit 6 Ni 32/22.
Plaintiff's Reply to the May 11, 2022 Response, dated Jul. 18, 2022, in the Munich Federal Patent Court, Nullity Suit 6 Ni 32/22.
Plaintiff's Response to Court Order disagreeing with Stay of Proceedings dated Oct. 28, 2022 in Mannheim District Court, Infringement suit 7 O 147/21.
Plaintiff's Technical Brief dated Sep. 29, 2022 in the Mannheim District Court, Infringement suit 7 O 147/21.
Plouin et al., Blood Pressure Outcome of Angioplasty in Atherosclerotic Renal Artery Stenosis: A Randomized Trial. Essai Multicentrique Medicaments vs Angioplastie (EMMA) Study Group, Hypertension 31, 823-29 (1998).
Prakash, Punit, et al., "Considerations for Theoretical Modeling of Thermal Ablation with Catheter-Based Ultrasonic Sources: Implications for Treatment Planning, Monitoring and Control," International Journal of Hyperthermia, 28:1, 69-86.
Prochnau, Dirk et al., Catheter-based renal denervation for drug-resistant hypertension by using a standard electrophysiology catheter, EuroIntervention, vol. 7, 1077-1080 (2012).
Pugsley, et al., The vascular system: An overview of structure and function, Journal of Pharmacological and Toxicological Methods 44 (2000) 333-340.
Pürerfellner, Helmut et al., Incidence, Management and Outcome in Significant Pulmonary Vein Stenosis Complicating Ablation for Atrial Fibrillation, 93 Am. J. Cardiol. 1428 (2004).
Pürerfellner, Helmut & Martinek, Martin, Pulmonary vein stenosis following catheter ablation of atrial fibrillation, 20 Curr. Opin. Cardiol. 484 (2005).
Reaz, M.B.I., et al., "Techniques of EMG signal analysis: detection, processing, classification and applications," Biological Procedures Online, Jan. 2006, 25 pages.
Reddy, Vivek Y., "Use of a Diode Laser Balloon Ablation Catheter to Generate Circumferential Pulmonary Venous Lesions in an Open-Thoracotomy Caprine Model," PACE, vol. 27, 52-57, Jan. 2004.
Romanes, G.J., Cunningham's Textbook of Anatomy (11th ed. 1972).
Ryan, Steve, What are the Risks Associated with a Pulmonary Vein Ablation Procedure?, Atrial Fibrillation: Resources for Patients (last accessed Oct. 18, 2022).
Ryan, Thomas et al., Proceedings of Thermal Treatment of Tissue with Image Guidance, Progress in Biomedical Optics, vol. 3594 (1999).
Ryan, Thomas P., Thermal Treatment of Tissue with Image Guidance; Ultrasound Catheters For Circumferential Cardiac Ablation 1999.
Sakakura, Kenichi et al., Anatomic Assessment of Sympathetic Peri-Arterial Renal Nerves in Man, Journal of the American College of Cardiology, vol. 64, No. 7, 635-643 (2014).
Salmanpour, A., L. J. Brown and J. K. Shoemaker, "Detection of Single Action Potential in Multi-Unit Postganglionic 7 Sympathetic Nerve Recordings in Humans: A Matched Wavelet Approach," 2010 IEEE International Conference on Acoustics, Speech and Signal Processing, Dallas, TX, 2010, pp. 554-557. doi: 10.1 109/ICASSP. 2010.5495604.
Sanchez-Quintana, Damian et al., How close are the phrenic nerves to cardiac structures? Implications for cardiac interventionalists, 16 J. Cardiovasc. Electrophysiol 309 (2005) ("Sánchez- Quintana").
Sato, Yu, et al., "Translational Value of Preclinical Models for Renal Denervation: a histological comparison of human versus porcine renal nerve anatomy," EuroIntervention, 18, e1120-e1128, 2023.

(56) References Cited

OTHER PUBLICATIONS

Schlaich, M.P. et al., "Renal Denervation: A Potential New Treatment Modality for Polycystic Ovary Syndrome," Journal of Hypertension, vol. 29, No. 5, pp. 991-996 201 1 . doi:10.1097/HJH.0b013e328344db3a.
Schmieder, Ronald E., Renal denervation in patients with chronic kidney disease: current evidence and future perspectives, Nephrol. Dial. Transplant. gfac189 (2022).
Schneider, Peter, Endovascular Skills: Guidewire and Catheter Skills for Endovascular Surgery, 2nd ed., Marcel Dekker, Inc., New York, NY (2003).
Schneider, Peter A., Endovascular Skills, Quality Medical Publishing, Inc., 1998 ("Schneider").
Schmidt, Boris, et al., "Pulmonary Vein Isolation by High Intensity Focused Ultrasound," Indian Pacing and Electrophysiology Journal, pp. 126-133 (2006).
Selected documents from the File History of Inter Partes Reexamination U.S. Appl. No. 95/002,110, exhibit to Petition for Inter Partes Review of U.S. Pat. No. 8,845,629, filed Jan. 13, 2022 in the Patent Trial and Appeal Board, United States Patent and Trademark Office, Petition No. PTAB-IPR2022-00431.
Shimizu, Kazumasa et al., Sympathetic Dysfunction in Heart Failure, Bailliere's Clinical Endocrinology and Metabolism, vol. 7, No. 2 (1993).
Shonai et al., Renal Artery Aneurysm: Evaluation with Color Doppler Ultrasonography Before and lifter Percutaneous Transarterial Embolization, J. Ultrasound Med. 19, 277-80 (2000)("Shonai 2000").
Slide deck from Medtronic Circulatory System Devices Panel Meeting, General Issues Panel: Clinical Evaluation of Anti-Hyperintensive Devices (Dec. 5, 2018).
Smithwick, R. H., et al., "Splanchnicectomy for essential hypertension." J. Am. Med. Assoc., 152:1501-1504 (1953).
Stella, A., et al. "Effects of reversible renal denervation on haemodynamic and excretory functions of the ipsilateral and contralateral kidney in the cat." J Hypertension, 4: 181-188 (1986)("Stella").
Stipulation Modifying Schedule, dated Dec. 30, 2022 in the Patent Trial and Appeal Board, United States Patent and Trademark Office, Petition No. PTAB-IPR2022-00431.
Stipulation Modifying Schedule, dated Feb. 16, 2023 in the Patent Trial and Appeal Board, United States Patent and Trademark Office, Petition No. PTAB-IPR2022-00431.
Stoeckel, D. et al., A Survey of Stent Designs, Min Invas Ther & Allied Technol 2002: 11(4) 137-147 (2002).
Swartz, John F. et al., Radiofrequency Endocardial Catheter Ablation of Accessory Atrioventricular Pathway Atrial Insertion Sites, 87 Circulation 487 (1993).
Tank, J. et al., "Spike Rate of Multi-Unit Muscle Sympathetic Nerve Fibers Following Catheter-Based Renal Nerve Ablation," J Am. Soc Hypertens, Oct. 2015; 9(10): 794-801. doi:10.1016/j.jash.2015.07.012.
Tanaka, Kazushi et al., "A New Radiofrequency Thermal Balloon Catheter for Pulmonary Vein Isolation," Journal of the American College of Cardiology vol. 38, No. 7, 2001.
Teigen et al., Segmental Renal Artery Embolization for Treatment of Pediatric Renovascular Hypertension, J. Vasco Interv. Radiol. 3, 111-7 (1992).
Thatipelli, Mallik R., et al., CT angiography of renal artery anatomy for evaluating embolic protection devices, 18 J. Vasc. Interv. Radiol. 842 (2007).
The Doctors and Experts at WebMD, Webster's New World Medical Dictionary (3rd ed. 2008) ("WebsterMD").
Transcript of the Mar. 2, 2023 deposition of Dr. John Moriarty.
Transcript of the Mar. 3, 2023 deposition of Dr. Chris Daft.
Transcript of deposition of the Jan. 1, 2023 deposition of Dr. Robert Tucker.
Transcript of the Jan. 14, 2023 deposition of Dr. Daniel van der Weide.
Transcript of the Sep. 30, 2022 deposition of Dr. Chris Daft.
Transcript of the Oct. 1, 2022 deposition of Dr. Farrell Mendelsohn.
Tsao, Hsuan-Ming et al., Evaluation of Pulmonary Vein Stenosis after Catheter Ablation of Atrial Fibrillation, 6 Card. Electrophysiol. Rev. 397 (2002).
Turner, et al., "Initial Experience Using the Palmaz Corinthian Stent for Right Ventricular Outflow Obstruction in Infants and Small Children", Catheterization and Cardiovascular Interventions 51:444-449 (2000).
Uchida, et al., "Effect of radiofrequency catheter ablation on parasympathetic denervation: A comparison of three different ablation sites." PACE, 21 :2517-2521 (1998).
Ulmsten, Ulf et al., "The Safety and Efficacy of MenoTreatTM, a new balloon device for thermal endometrial ablation," Acta Obstet Gynecol Scand 2001; 80: 52-57.
Vaezy, Shahram et al., Image-Guided Acoustic Therapy, Annual Review Biomedical Engineering, vol. 3, 375-390 (2001).
Valente, John F et al., Laparoscopic renal denervation for intractable ADPKD-related pain, 16 Nephrol. Dial. Transplant. 160 (2001).
Vujaskovic, Z. et al., (1994) Effects of intraoperative hyperthermia on canine sciatic nerve: histopathologic and morphometric studies, International Journal of Hyperthermia, 10:6, 845-855 (1994) ("Vujaskovic 1994").
Wanchoo, Nishey, Medtronic Gets European and Australian Approval for Symplicity Spyral Multi-Electrode Renal Denervation Catheter, Medgadget (2013).
Weinstock, Marta et al., "Renal Denervation Prevents Sodium Retention and Hypertension in Salt- Sensitive Rabbits with Genetic Baroreflex Impairment", 90 Clinical Science 287 (1996).
Xu, J. et al., "A Bidirectional Neuromodulation Technology for Nerve Recording and Stimulation, Micromachines," vol. 9, 1 1 538. Oct. 23, 2018. doi:10.3390/mi9110538.
Xu, J., T. Wu and Z. Yang, "A New System Architecture for Future Long-Term High-Density Neural Recording," IEEE Transactions on Circuits and Systems II: Express Briefs, vol. 60, No. 7, pp. 402-406, Jul. 2013. doi:10.1109/ TCSII.2013.2258270.
Zazgornik, "Bilateral Nephrectomy: The best, but often overlooked, treatment for refractory hypertension in hemodialysis patients," Am. J. Hypertension, 11:1364-1370 (1998).
Ziegler et al., Sources of Urinary Catecholamines in Renal Denervated Transplant Recipients, 8 J. Hypertension No. 10, 927 (1990).
U.S. Appl. No. 17/453,636, filed Nov. 4, 2021, File History.
U.S. Appl. No. 10/408,665, File History.
U.S. Appl. No. 60/624,793, File History.
U.S. Appl. No. 60/370,190, File History.
U.S. Appl. No. 60/415,575, File History.
U.S. Appl. No. 60/442,970, File History.
U.S. Appl. No. 60/616,254, File History.
U.S. Appl. No. 60/747,137, File History.
U.S. Appl. No. 60/808,306, File History.
U.S. Appl. No. 60/816,999, File History.
U.S. Appl. No. 61/405,472, File History.
U.S. Appl. No. 11/532,814, Non-Final Office Action mailed Mar. 29, 2012.
U.S. Appl. No. 15/261,732, Notice of Allowance dated Sep. 25, 2018.
U.S. Appl. No. 16/219,874, Final Office Action mailed Dec. 21, 20, 7 pages.
U.S. Appl. No. 16/517,180, Preliminary Amendment filed Jul. 19, 2019, 12 pgs.
File History of U.S. Appl. No. 12/754,337.
File History to U.S. Pat. No. 9,943,666.
File History to U.S. Pat. No. 9,981, 108.
File History to U.S. Pat. No. 10,039,901.
Final Office Action dated Feb. 19, 2021, U.S. Appl. No. 15/996,978, filed Jun. 4, 2018.
Final Office Action dated Jun. 16, 2021, U.S. Appl. No. 15/996,978, filed Jun. 4, 2018.
Non-Final Office Action dated Sep. 2, 2021, U.S. Appl. No. 15/996,978, filed Jun. 4, 2018.
Notice of Allowance dated Oct. 6, 2021, U.S. Appl. No. 15/996,978, filed Jun. 4, 2018.
Response to Office Action dated May 18, 2021, U.S. Appl. No. 15/996,978, filed Jun. 4, 2018.

(56) References Cited

OTHER PUBLICATIONS

Response to Office Action dated Jul. 20, 2021, U.S. Appl. No. 15/996,978, filed Jun. 4, 2018.
Response to Office Action dated Sep. 22, 2021, U.S. Appl. No. 15/996,978, filed Jun. 4, 2018.
Borchert, Bianca et al., "Lethal Atrioesophageal Fistual After Pulmonary Vein Isolation using High-Intensity Focused Ultrasound (HIFU)" J. Hrthm vol. 5, Issue 1, p. 145-148, Jan. 2008.
Calkins, Hugh et al., "Temperature Monitoring During Radiofrequency Catheter Ablation Procedures Using Closed Loop Control," Circulation vol. 90, No. 3, p. 1279-1286, Sep. 1994.
Deardorff, Dana L. et al., "Control of interstitial thermal coagulation: Comparative evaluation of microwave and ultrasound applicators," Medical Physics vol. 28, No. 1, p. 104-117, Jan. 2001.
Dinerman, Jay L. et al., "Temperature Monitoring During Radiofrequency Ablation," Journal of Cardiovascular Electrophysiology, vol. 7 No. 2, p. 163-173, Feb. 1996.
Esler, Murray et al., "The future of renal denervation," Autonomic Neuroscience: Basic and Clinical, vol. 204, p. 131-138, May 2017.
Filonenko, E.A. et al., "Heating of Biological Tissues by Two-Dimensional Phased Arrays with Random and Regular Element Distributions," Acoustical Physics, vol. 50 No. 2, p. 222-231, 2004.
Fry, William J., "Action of Ultrasound on Nerve Tissue—A review," The Journal of the Acoustical Society of America, vol. 25 No. 1, p. 1-5, Jan. 1953.
Fry, Frank J., "Precision High Intensity Focusing Ultrasonic Machines for Surgery," High Intensity Focused U.S., 152-156, Sep. 6-7, 1957.
Haines, David, "Biophysics of Ablation: Application to Technology," Journal of Cardiovascular Electrophysiology, vol. 15, No. 10, p. S2-S11, Oct. 2004.
Hynynen, K. et al., "Design of Ultrasonic Transducers for Local Hyperthermia," Ultrasound in Med. & Biol., vol. 7, No. 4, p. 397-402, Feb. 1981.
Hynynen, K. et al., "Temperature measurements during ultrasound hyperthermia," Medical Physics vol. 16, No. 4, p. 618-626, Jul./Aug. 1989.
Jolesz, Ferenc A. et al., "MR Imaging-Controlled Focused Ultrasound Ablation: A Noninvasive Image-Guided Surgery," Magnetic Resonance Imaging Clinics of North America, vol. 13, Issue 3, p. 545-560, 2005.
Kandzari, David A., et al., "Reply to letter to the editor by Kintur Sanghvi, MD; Allen McGrew, DO; and Kiran Hegde, BE, MBA," American Heart Journal, vol. 180, p. e3-e4, Oct. 2016.
Lafon, C. et al., "Design and Preliminary Results of an Ultrasound Applicator for Interstitial Thermal Coagulation," Ultrasound in Medicine & Biology, vol. 24, No. 1, p. 113-122, 1998.
Lewis, Matthew A. et al., "Thermometry and Ablation Monitoring with Ultrasound," Int. J. Hyperthermia vol. 31, Issue 2, p. 163-181, Mar. 2015.
Liu, Xinmeng et al., "Visualization and mapping of the right phrenic nerve by intracardiac echocardiography during atrial fibrillation ablation," Europace vol. 25, p. 1352-1360, 2023.
Mendelsohn, Farrell O., "Microanatomy of the Renal Sympathetic Nervous System," Endovascular Today, p. 59- 62, Oct. 2013.
Okamura, Keisuke et al., "Intravascular Ultrasound Can Be Used to Locate Nerves, but not Confirm Ablation, During Renal Sympathetic Denervation," J. Clin. Med. Res., vol. 13, No. 12, p. 556-562, 2021.
Quadri, Syed A. et al., "High-intensity focused ultrasound: past, present, and future in neurosurgery," Neurosurgical Focus, vol. 44, No. 2, p. 1-9, Feb. 2018.
Ross, Anthony B. et al., "Highly directional transurethral ultrasound applicators with rotational control for MRI-guided prostatic thermal therapy," Physics in Medicine & Biology, vol. 49, p. 189-204, Jan. 2004.
Sakaoka, Atsushi, et al., "Accurate Depth of Radiofrequency-Induced Lesions in Renal Sympathetic Denervation Based on a Fine Histological Sectioning Approach in a Porcine Model," Cir. Cardiovasc. Interv., vol. 11, p. 1-8, 2018.
Sanghvi, Kintur et al., "Rationale and design for studies of renal denervation in the absence (Spyral HTN Off-Med) and presence (Spyral HTN On-Med) of antihypertensive medications," American Heart Journal, vol. 180, p. e1-e2. Oct. 2016.
Satou, Shunsuke et al., "Observation of renal sympathetic nerves by intravascular ultrasound," Hypertension Research vol. 42, p. 1092-1094, 2019.
Schmidt, Boris et al., "Balloon Catheters for Pulmonary Vein Isolation," Herz vol. 33, p. 580-584, 2008.
Smith, Nadine Barrie et al., "Transrectal Ultrasound Applicator for Prostate Heating Monitored Using MRI Thermometry," Int. J. Radiation Oncology Biol. Phys. vol. 43, No. 1, p. 217-225, 1998.
Stauffer, P.R et al., "13 Interstitial Heating Technologies," Thermoradiotherapy and Thermochemotherapy, p. 279-320, 1995.
Swanson, David K. et al., "Tissue temperature Feedback Control of Power, The Key to Successful Ablation," Innovations, vol. 6 No. 4, p. 276-282, Jul./Aug. 2011.
Tabei, Makoto et al., "A k-space method for coupled first-order acoustic propagation equations," J. Acoust. Soc. Am., vol. 111, No. 1, pt. 1, p. 53-63, Jan. 2002.
Tzafriri, Abraham R. et al., "Innervation Patterns May Limit Response to Endovascular Renal Denervation," Journal of the American College of Cardiology, vol. 64, No. 11, p. 1079-1087, Sep. 2014.
Umemura, Shin-ichiro, "Focused ultrasound transducer for thermal treatment," International Journal of Hyperthermia, vol. 31, No. 2, p. 216-221, 2015.
Wan, Hong et al., "Thermal Dose Optimization for Ultrasound Tissue Ablation," IEE Transactions on Ultrasonics, Ferroelectrics, and Frequency Control, vol. 46, No. 4, p. 913-928, Jul. 1999.
Zivin, Adam, et al., "Temperature Monitoring versus Impedance Monitoring during RF Catheter Ablation," Radiofrequency Catheter Ablation of Cardiac Arrhythmias, Basic Concepts and Clinical Applications, Second Edition, Edited by Shoei K. Stephen Huang, MD & David J. Wilber, MD, p. 103-112, 2000.

* cited by examiner

INTRALUMINAL MICRONEUROGRAPHY DENERVATION PROBE WITH RADIO FREQUENCY ABLATION

CROSS-REFERENCE TO RELATED APPLICATIONS

This application is a continuation application of U.S. application Ser. No. 16/517,180, filed Jul. 19, 2019, which is a continuation Ser. No. 15/299,694, filed Oct. 21, 2016, which is a continuation of U.S. application Ser. No. 15/204,349, filed Jul. 7, 2016, which claims the benefit of U.S. Provisional Application No. 62/198,382, filed Jul. 29, 2015, all of which are incorporated herein by reference in their entireties to provide continuity of disclosure.

FIELD

The invention relates generally to neural measurement, and more specifically to an intraluminal microneurography probe with radio frequency or microwave ablation.

BACKGROUND

The human body's nervous system includes both the somatic nervous system that provides sense of the environment (vision, skin sensation, etc.) and regulation of the skeletal muscles, and is largely under voluntary control, and the autonomic nervous system, which serves mainly to regulate the activity of the internal organs and adapt them to the body's current needs, and which is largely not under voluntary control. The autonomic nervous system involves both afferent or sensory nerve fibers that can mechanically and chemically sense the state of an organ, and efferent fibers that convey the central nervous system's response (sometimes called a reflex arc) to the sensed state information. In some cases, the somatic nervous system is also influenced, such as to cause vomiting or coughing in response to a sensed condition.

Regulation of the human body's organs can therefore be somewhat characterized and controlled by monitoring and affecting the nerve reflex arc that causes organ activity. For example, the renal nerves leading to the kidney can often cause a greater reflexive reaction than desired, contributing significantly to hypertension. Measurement of the nerve activity near the kidney, and subsequent ablation of some (but not all) of the nerve can therefore be used to control the nervous system's overstimulation of the kidney, improving operation of the kidney and the body as a whole.

Because proper operation of the nervous system is therefore an important part of proper organ function, it is desired to be able to monitor and change nervous system function in the human body to characterize and correct nervous system regulation of internal human organs.

SUMMARY

One example embodiment of the invention comprises an intraluminal microneurography probe, having a probe body that is substantially cylindrical and that is configured to be introduced into an artery near an organ of a body without preventing the flow of blood through the artery. An expandable sense electrode is fixed to the probe body at one end of the sense electrode and is movable relative to the probe body at a second end of the sense electrode such that movement of the movable end toward the fixed end causes the sense electrode to expand from the probe body toward a wall of the artery, and an expandable stimulation electrode is fixed to the probe body at one end of the stimulation electrode and movable relative to the probe body at a second end of the stimulation electrode such that movement of the movable end toward the fixed end causes the sense electrode to expand from the probe body toward a wall of the artery. A radio frequency ablation element is configured to ablate nerve tissue in the vicinity of the expandable sense and stimulation electrodes. A ground electrode is configured to couple to the body, and a plurality of electrical connections are operable to electrically couple at least the expandable sense electrode, expandable stimulation electrode, ground electrode, and radio frequency ablation element to electrical circuitry.

In further examples, the radio frequency ablation element comprises one or more monopole, dipole, loop, or ring antennas, or a phase-steered array of antennas. In further examples, the probe further comprises at least one of a cooling element configured to cool the probe in the vicinity of the radio frequency ablation element, and a reflector or shield configured to direct energy from the radio frequency ablation element in a specific direction.

In another example nerve activity associated with a body organ is characterized by introduction of a probe into artery to a location proximate to the body organ, and expansion of an expandable sense electrode and an expandable stimulation electrode comprising a part of the probe to contact the artery wall while permitting blood flow around the expanded sense and stimulation electrodes. An electricity source coupled to the stimulation electrode is used to excite the stimulation electrode, and the expanded sense electrode is used to measure sympathetic nerve activity as a result of exciting the stimulation electrode. A radio frequency ablation element is used to ablate nerves in the vicinity of the location proximate to the body organ such as via a radio frequency ablation element comprising a part of the probe, and re-excitation of the stimulation electrode using an electricity source coupled to the stimulation electrode, and re-measurement of sympathetic nerve activity as a result of exciting the stimulation electrode using the expanded sense electrode are performed to confirm the effects of the ablation.

The details of one or more examples of the invention are set forth in the accompanying drawings and the description below. Other features and advantages will be apparent from the description and drawings, and from the claims.

DETAILED DESCRIPTION

Figure 1:
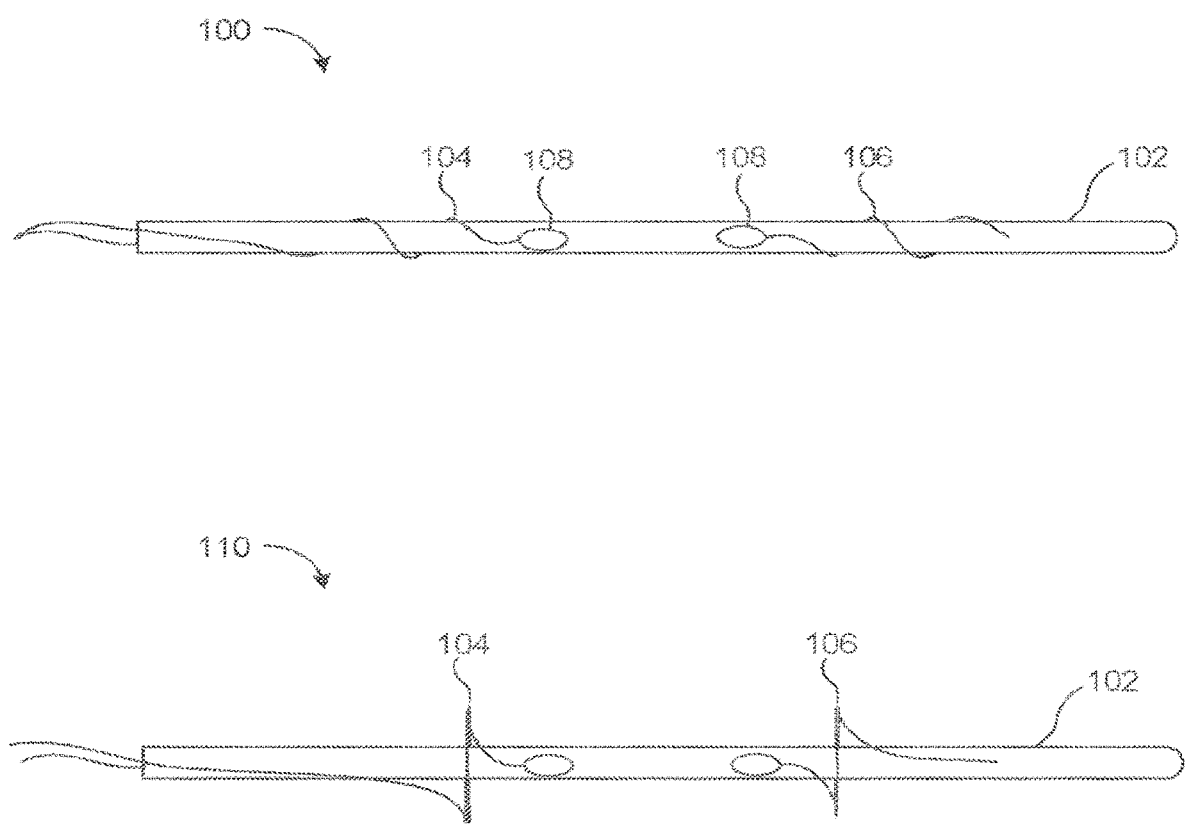
FIG. 1 illustrates an intraluminal microneurography probe having expandable helical wire electrodes, consistent with an example.

In the following detailed description of example embodiments, reference is made to specific example embodiments by way of drawings and illustrations. These examples are described in sufficient detail to enable those skilled in the art to practice what is described, and serve to illustrate how elements of these examples may be applied to various purposes or embodiments. Other embodiments exist, and logical, mechanical, electrical, and other changes may be made. Features or limitations of various embodiments described herein, however important to the example embodiments in which they are incorporated, do not limit other embodiments, and any reference to the elements, operation, and application of the examples serve only to define these example embodiments. Features or elements shown in various examples described herein can be combined in ways other than shown in the examples, and any such combination is explicitly contemplated to be within the scope of the examples presented here. The following detailed description does not, therefore, limit the scope of what is claimed.

Regulating operation of the nervous system to characterize and improve organ function includes in some examples introduction of a probe such as a needle, catheter, wire, or the like into the body to a specified anatomical location, and partially destroying or ablating nerves using the probe to destroy nerve tissue in the region near the probe. By reducing nerve function in the selected location, an abnormally functioning physiological process can often be regulated back into a normal range.

Unfortunately, it is typically very difficult to estimate the degree to which nerve activity has been reduced, which makes it difficult to perform a procedure where it is desired to ablate some, but not all nerves to bring the nervous system response back into a desired range without destroying the nervous system response entirely.

One such example is renal nerve ablation to relieve hypertension. Various studies have confirmed that improper renal sympathetic nerve function has been associated with hypertension, and that ablation of the nerve can improve renal function and reduce hypertension. In a typical procedure, a catheter is introduced into a hypertensive patient's arterial vascular system and advanced into the renal artery. Renal nerves located in the arterial wall and in regions adjacent to the artery are ablated by destructive means such as radio frequency waves, ultrasound, laser or chemical agents to limit the renal sympathetic nerve activity, thereby reducing hypertension in the patient.

Unfortunately, renal nerve ablation procedures are often ineffective, such as due to either insufficiently ablating the nerve or destroying more nerve tissue than is desired. Clinicians often estimate based on provided guideline estimates or past experience the degree to which application of a particular ablative method will reduce nerve activity, and it can take a significant period of recovery time (3-12 months) before the effects of the ablation procedure are fully known.

Some attempt has been made to monitor nerve activity in such procedures by inserting very small electrodes into or adjacent to the nerve body, which are then used to electrically monitor the nerve activity. Such microneurography practices are not practical in the case of renal ablation because the renal artery and nerves are located within the abdomen and cannot be readily accessed, making monitoring and characterization of nerve activity in a renal nerve ablation procedure a challenge.

Prior methods such as inserting electrodes into the arteries of a patient's heart and analyzing received electrical signals are not readily adaptable to renal procedures, as arteries in the heart are generally large and more readily accommodate probes for performing such measurements. Further, the cardiac electrical signals emitted from the heart are generally large and slow-moving relative to electrical signals near the renal arteries, which tend to be smaller in size and produce smaller signals that propagate more quickly through the nerves. As such, intravascular techniques used in heart measurements are readily adaptable to similar renal processes.

Because nerve activity during organ procedures such as renal nerve ablation cannot be readily measured, it is also difficult to ensure that an ablation probe is located at the most appropriate sites along the renal artery, or to measure the efficiency of the nerve ablation process in a particular patient.

Some examples presented herein therefore provide an improved probe and method for characterizing nerve activity near an organ such as a kidney, including electrodes configured specifically to measure nerve activity in an environment different from the heart while permitting blood flow around the probe. In a more detailed example, the probe includes a sense electrode and a stimulation electrode that are expandable from a body of the probe, which can be introduced via a sheath. The sheath in a further embodiment comprises one or more electrodes, such as one or more sense electrode reference or ground electrodes.

FIG. 1 illustrates an example of such a probe. Here, a probe assembly is shown generally at 100, including probe body 102, and first and second helical electrodes 104 and 106. Each of the helical electrodes is attached to the probe body at one end, shown here as an attachment point 108, such as an epoxy bead or other suitable attachment mechanism. The opposite end of each of the helical electrodes is constrained in the example shown, such as by emerging through a hole in the probe as shown by helical electrode 106, and extends from the left end of the probe assembly to connect to electronic instrumentation to perform various functions. The configuration of the helical electrode wires is such that the wires will expand about the axis of the probe body 102 when the wire of each helical electrode is forced toward the attachment points 108, causing the wire to form a circular shape having a diameter substantially larger than the helical electrode wires in the collapsed position, as shown at 100.

The probe assembly is shown again at 110, here with the helical electrode wires 104 and 106 forced toward the attachment points 108, causing the wire to expand away from the probe body 102. This helical expansion allows the helical electrodes to expand in an environment such as an artery such as to contact the artery walls while allowing blood to flow around the probe body 102 and past the helical electrodes 104 and 106.

Figure 2:
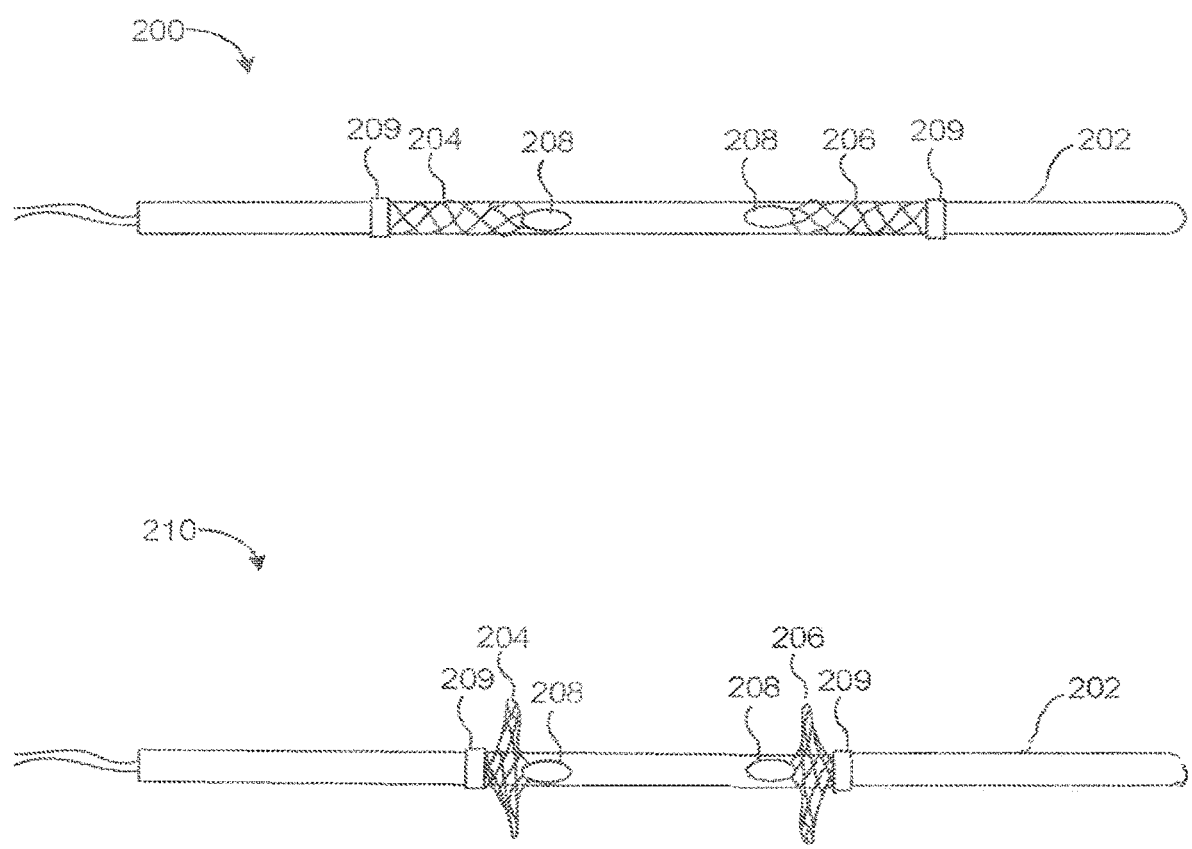
FIG. 2 illustrates an intraluminal microneurography probe having expandable wire mesh electrodes, consistent with an example.

Another example of a probe configured to characterize nerve activity near an organ such as a kidney while permitting blood flow around the probe is shown in FIG. 2. Here, a probe body is shown at 202, having mesh electrodes 204 and 206 affixed thereto at attachment points 208. The mesh electrodes are substantially similar to the helical wire electrodes of FIG. 1, except that several such electrodes are interwoven to form a mesh that is closely wrapped around the probe body 202. In this example, each mesh electrode also has a sliding collar element 209 located at the end of the mesh electrode opposite attachment point 208.

This sliding collar 209 when moved toward the attachment point 208 causes the mesh to expand around the probe body 202, as shown generally at 210. Here, the expanded mesh electrodes 204 and 206 are configured to provide electrical contact, such as with an artery wall, in a diameter significantly larger than the diameter of the probe body 202. This enables insertion of the probe body into an artery, and expansion of the electrodes 204 and 206 to contact the artery walls, without blocking blood flow through the artery. Although the examples of FIGS. 1 and 2 show two probe configurations that can achieve such functions, probe configurations other than those shown here may also be configured to achieve these or similar functions.

Figure 3:
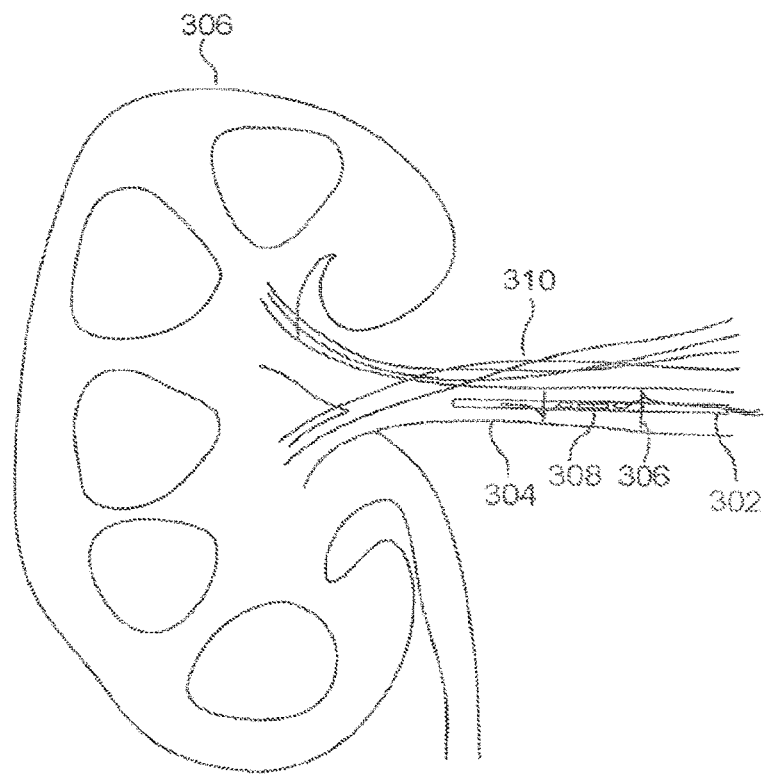
FIG. 3 shows introduction of an intraluminal microneurography probe into an artery in a location near a kidney, consistent with an example.

FIG. 3 illustrates one example of use of such a probe, in which a probe 302 such as that shown in FIG. 1 or FIG. 2 is introduced into a blood vessel, such as an artery 304, in a location near a body organ such as kidney 306. The probe is introduced via a sheath in some examples, such as where a sheath is advanced to the intended probe location in the artery, and then withdrawn sufficiently to expose the probe 302 to the artery 304. The probe 302 here comprises a stimulation electrode such as electrodes 104 and 204 of FIGS. 1 and 2, and a sense electrode such as electrodes 106 and 206 of the same Figures.

When deployed, the electrodes are expanded as shown at 308, such that they are near or touch the walls of the artery 304. The electrodes are thereby located nearer the nerve bundle 310 connecting the kidney to the central nervous system, as the nerve bundle tends to approximately follow the artery leading to most body organs. As shown at 310, the nerve bundle tends to follow the artery more closely at the end of the artery closer to the kidney, while spreading somewhat as the artery expands away from the kidney. As a result it is desired in some examples that the probe is small enough to introduce relatively near the kidney or other organ, as nerve proximity to the artery is likely to be higher nearer the organ.

When in place, a practitioner can use instrumentation coupled to the sense electrode and stimulation electrode to stimulate the nerve, and monitor for nerve response signals used to characterize the nervous system response to certain stimulus. In a further example, an ablation element 308 is configured to ablate nerve tissue, such as by using radio frequency, ultrasound, or other energy, such that the probe can actively stimulate the nerve and sense resulting neural signals in between applications of energy via the ablation element 308, enabling more accurate control of the degree and effects of nerve ablation. In other examples, a probe 302 lacking an ablation element can be remove via the sheath, and an ablation probe inserted, with the ablation probe removed and the probe 302 reinserted to verify and characterize the effects of the ablation probe.

Figure 4:
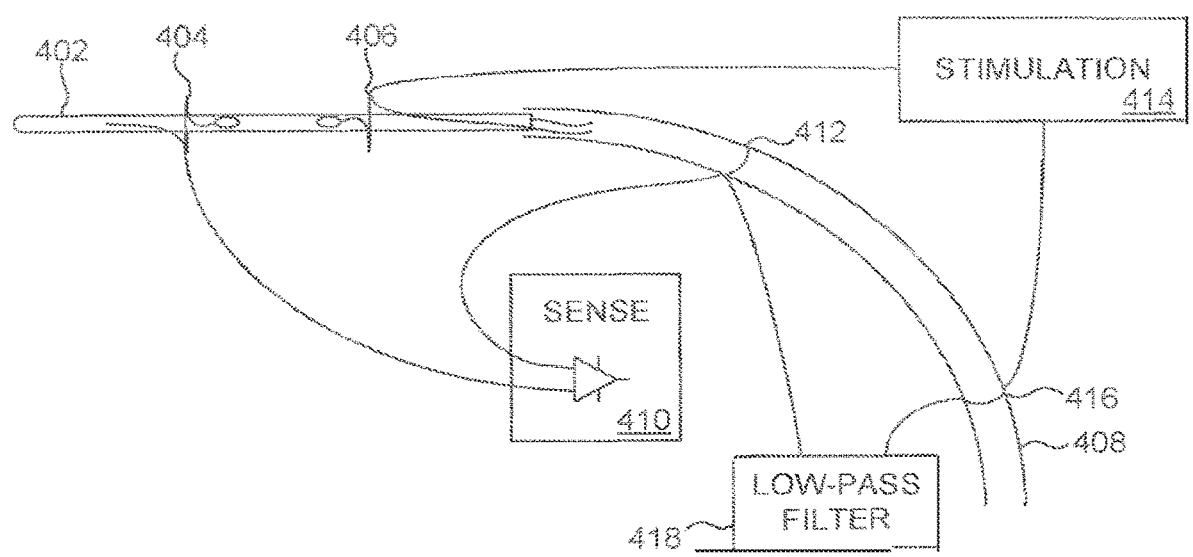
FIG. 4 shows an intraluminal microneurography probe and sheath assembly coupled to associated instrumentation, consistent with an example.

FIG. 4 shows an intraluminal microneurography probe and sheath assembly coupled to associated instrumentation, consistent with an example. Here, a probe body 402 has an expandable sense electrode 404 and an expandable stimulation electrode 406, couple via wires to instrumentation. A sheath 408 is used to introduce the probe into an artery or other biological lumen or suitable location, and to carry instrumentation wires and mechanical connections used to manipulate the expandable electrodes. The electrodes are not shown here running through the sheath, but are instead shown as schematic links between the electrodes and various instrumentation circuitry for clarity.

In this example, the expandable sense electrode 404 is coupled to a sense circuit, such as a differential amplifier as shown at 410, with the other input to the sense amplifier circuit coupled to a ground electrode such as local ground electrode 412 coupled to the sheath 408. In another example, local ground electrode is located elsewhere, such as on the probe body 404. The expandable stimulation electrode 406 is similarly coupled to a stimulation circuit 414 that is operable to provide a stimulation voltage or current signal of a desired pulse shape, intensity, and duration to the expandable stimulation electrode 406, with reference to body ground. Body ground is established in this example by a body ground electrode 416, which is here also shown as coupled to the sheath 408, but which in other embodiments will take other forms such as an electrode coupled to the body's skin. Here, the body ground electrode 416 is further coupled to the local ground electrode 412 by use of a low pass filter, having a frequency response or time constant selected such that the local ground electrode does not drift significantly from the body ground level but retains the ability to accurately detect and characterize local nerve impulses.

The electrodes in this example comprise electrical wires that are significantly smaller than are used in other applications such as cardiac probes, in part because the pulse duration in the nerve bundle leading to most body organs is typically much shorter than a cardiac muscle excitation signal. In one embodiment, the sense electrode 404 therefore comprises a wire or mesh of wires having a diameter of 8-10 thousandths of an inch, while in other examples the wire diameter is 5-10 thousandths, 5-15 thousandths, or any size under 15, 10, 8, or 5 thousandths of an inch. The sense electrode is thereby configured to accurately detect a typical nerve action potential of 2 milliseconds traveling at a meter per second without smearing or distorting the measured pulse due to an overly large electrode.

The stimulation electrode in various examples comprises a wire or mesh of wires having any of the above sizes, but in another example, it is desired that the stimulation electrode 406 be substantially larger than the sense electrode 404 to avoid hyperpolarization of the nerve in the region of the electrode during stimulation.

Wire size of electrodes such as the sense electrode 404 is selected in further examples based on a typical nerve conduction velocity range of 0.4-2 meters/second, with nerve impulses ranging from 1-3 milliseconds. Also, the sense electrode 404 and stimulation electrode 406 are desirably placed a sufficient distance apart, such as 3 centimeters, to accurately detect a typical nerve action potential of 2 milliseconds without interference from the stimulation electrode.

Because the size of organ arteries such as the renal artery are typically in the range of 5 millimeters in diameter, it is desired to have a probe body that is a fraction of this size, such as having a diameter of 2.5 mm, 2 mm, 1 mm, or similar. This enables introduction of the probe without interfering with blood flow through the artery, such that the expandable electrodes can still expand to the artery walls without further significantly impeding blood flow.

Figure 5:
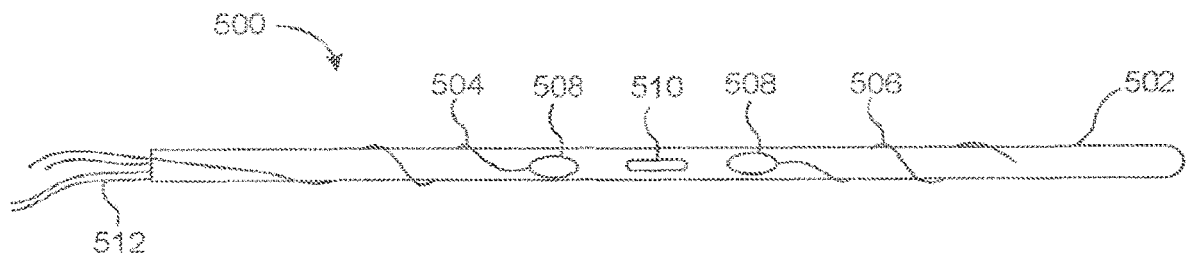
FIG. 5 shows an intraluminal microneurographic probe having an RF ablation antenna, consistent with an example.

FIG. 5 shows an intraluminal microneurographic probe having an RF ablation antenna, consistent with an example. The probe 500 in this example has a probe body 502 and first and second helical electrodes 504 and 506 as in the previous examples, and each of the helical electrodes is again attached to the probe body at one end as shown at 508. A Radio Frequency (RF) ablation antenna, such as a microwave antenna, is shown at 510, such as is shown at 308 in FIG. 3. The RF ablation antenna 510 is connected to a signal source using coaxial cable 512, such that the probe can actively stimulate the nerve and sense resulting neural signals using helical electrodes 504 and 506 in between applications of energy via the ablation element RF ablation antenna 510, providing more accurate control of the degree and effects of nerve ablation. The RF ablation antenna in various examples comprises a coil, a monopole or dipole, a reflector, a slot, a feedhorn, one or more rings, or combination of such elements to control ablation direction and heating in the region of the antenna. In another example, a cooling element such as a liquid jacket or tube is provided to cool tissue not targeted by the RF ablation antenna, and in some examples to shield RF energy from such tissue.

Figure 6:
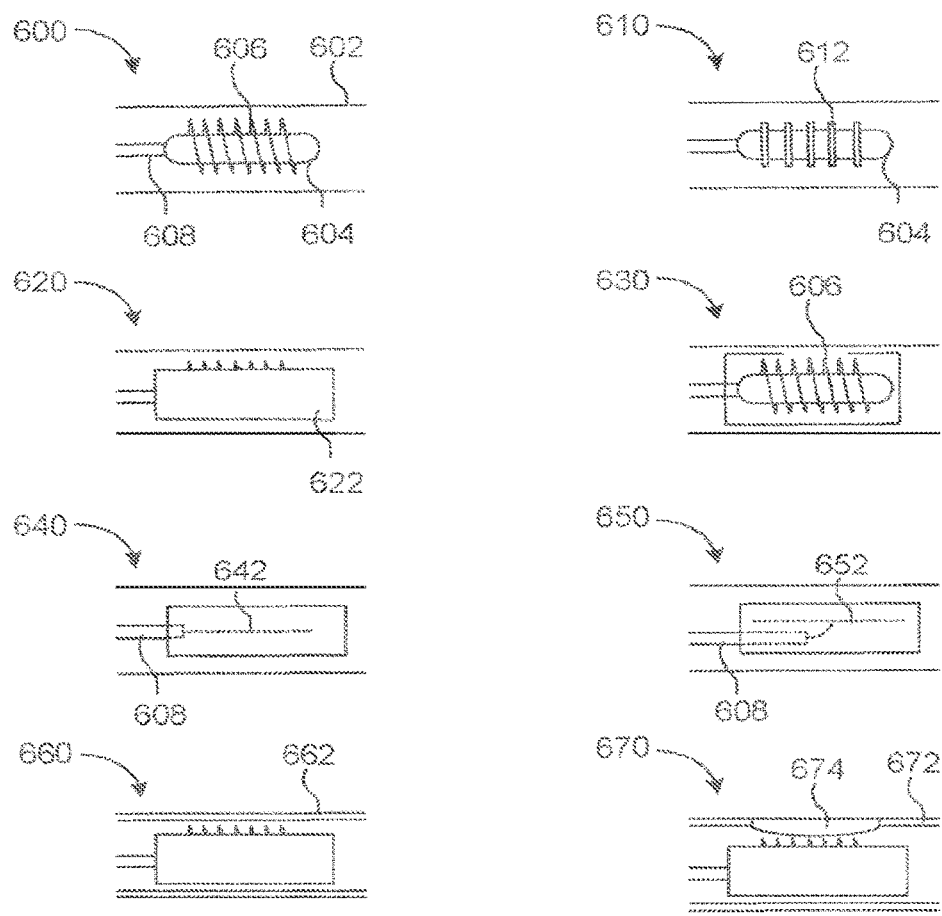
FIG. 6 shows a variety of RF ablation antenna configurations for an intraluminal microneurographic probe, consistent with various examples.

FIG. 6 shows RF ablation antenna configurations for an intraluminal microneurographic probe, consistent with various examples. In the example shown at 600, a probe body 602 includes an RF microwave ablation element having a core 604, and a coil element 606 coupled to a coaxial cable 608. In this example, the coil 606 serves as the microwave antenna, and in various examples it is wound, around a ferrite or other ferromagnetic core, oriented differently than as shown, or shielded to restrict the direction of RF emission.

Another example microwave antenna configuration is shown at 610, in which a core 604 includes two or more rings or windings 612 that are spaced at least a fraction of a wavelength apart from one another. The phase of the signal provided to the two or more windings 612 can therefore be varied to control the radiation pattern of the microwave antenna, directing energy to adjacent tissue as desired. In a more detailed example, the phase, frequency, or other parameters of the energy supplied to the windings is controlled such as in a phase-steered, array to target tissue at a certain depth or distance from the microwave probe for ablation.

Because the radiation pattern of the microwave antennas shown at 600 and 610 is approximately the same around the circumference of probe body 602, the example microwave antenna shown at 620 further comprises a reflector 622. Here, the reflector 622 wraps around the sides and bottom of the side view of the coil antenna as shown at 600, absorbing or reflecting radiation that is not directed upward as shown. This enhances the microwave antenna's capacity to target specific tissue, such as nerves, that are present in a known direction from the probe body 602.

In a similar example, the microwave antenna configuration shown at 630 includes a coil antenna 606 such as was shown at 600, but also includes a shield 632 around the antenna having an aperture 634 on the side of the shield configured to let radiation pass. The size, position, and other configuration parameters of the aperture 634 are therefore configured to pass radiation in the direction of nerve tissue to be ablated, while shielding radiation from being emitted in other directions unnecessarily. Combining technologies such as shielding and phase steering can be used in a further example to control both the direction and depth of emitted radiation, targeting tissue with greater discrimination than a simple coil antenna such as that shown at 600.

The microwave antenna in other examples comprises a configuration other than a coil or coils, such as a monopole or dipole antenna. A monopole microwave antenna is shown in the example at 640, where a coaxial cable 608 is coupled to an antenna element 642. Here, the coaxial cable is connected to one end of the antenna element 642, and the coaxial cable provides microwave energy to the antenna to ablate nearby nerve tissue. The frequency of the microwave energy and the antenna are typically configured so that the antenna is a quarter wavelength or longer relative to the microwave energy being provided.

At 650, a dipole antenna 652 is similarly configured, coupled to the coaxial cable and to a microwave power source in the center of the antenna 652 rather than at one end. This configuration makes the antenna 652 a dipole antenna rather than a monopole as shown at 640/642. Although the radiation pattern from a monopole antenna is primarily perpendicular to the antenna, it can vary in width and have lobes at varying angles from perpendicular depending on the wavelength of the microwave energy signal provided and the length of the antenna. The dipole antenna shown at 650/652 can be configured to have a single, narrow lobe of radiated energy perpendicular to the antenna which may be of greater value in targeting tissue for ablation. In a further example, multiple monopole or dipole antenna elements are provided, such as shown at 610, and phase steering or other such methods are used to enhance control over the direction and depth of radiated microwave power.

Because the nerve or other tissue being ablated is typically on only one side of the probe body 602, shields or apertures such as those shown at 620 and 630 may be employed with various microwave antenna configurations to limit emission of RF energy to the direction of the tissue to be ablated. Because microwave antennas can cause significant heating in tissue surrounding the antenna, some probe examples also include one or more cooling elements, such as a coolant jacket in the vicinity of the microwave antenna. At 660, an antenna with a shield such as is shown at 620 is provided, along with a probe body having both an inner and outer wall forming a cooling jacket 662. The cooling jacket in this example reduces heating from the antenna in the region immediately surrounding the probe body, such as from a heated antenna coil or other element, or from a reflector or shield. In a more detailed example, cooling fluid is circulated within the cooling jacket, such as by a cooling fluid pump feeding coolant to the probe assembly.

In another example shown at 670, a probe assembly has a cooling jacket 672 that does not extend around the entire probe body in the vicinity of the microwave antenna. In a more detailed example, the cooling jacket 672 is interrupted by probe body portion through which coolant does not flow, such as the cooling jacket aperture shown at 674. In a further example, the cooling jacket comprises a metallic material that can also shield microwave energy from traversing through the cooling jacket, while the cooling jacket aperture 674 comprises a material that not metallic and that allows microwave energy to be emitted through that portion of the probe body. Such a configuration provides for selective microwave radiation in the desire direction, and also places cooling fluid or other cooling elements in close contact with metallic shield portions of the probe to more effectively cool the metallic shield elements.

An intraluminal microneurography probe such as those shown in FIGS. 1-6 can be introduced into an artery via a sheath, and used to monitor nerve activity during normal operation of an organ. This enables characterization of nerve activity in the organ, such as to diagnose or treat a variety of conditions. In one such example, a probe is used for characterization of overactive nerves reaching the kidney in patients suffering from hypertension, and to monitor ablation of the nerves to a point where nerve activity is in the desired range as measured using the probe. In other examples, the probe may be used while other actions are performed, such as to monitor nerve activity to a patient's prostate while surgery or other methods remove material to treat prostate cancer or enlarged prostate problems. Because it is desirable that significant nerve connection to the prostate be preserved during such procedures, a probe such as those presented here can be used to minimize the chances of nerve damage that may affect normal function of the prostate.

A probe such as those shown here can also be used to diagnose various organ dysfunctions, such as where an organ overreacts to nerve impulses or overstimulates the nerve in response to organ activity. The probe is here described in some examples as an intraluminal probe, meaning the probe may be introduced into various lumina or pathways in the body, such as arteries, veins, the gastrointestinal tract, pathways of bronchii in the lungs, pathways of the genitourinary tract, and other such pathways. The probe is neurographic in the sense that it enables characterization, such as measurement, recording, and visualization of neurologic activity in the vicinity of the probe. Because the autonomic nervous system regulates a wide variety of functions within the body, including circulation, digestion, metabolism, respiration, reproduction, etc. by a network of parasympathetic and sympathetic nerves that typically accompany the blood vessels supplying blood to the organs they regulate, an intraluminal neurographic probe such as those described here can be used to measure or characterize the regulation of many of these functions by introducing the probe into the blood vessels near the organ of interest.

Although the example of FIG. 3 illustrates ablation of nerves near the kidney to regulate kidney function in treating hypertension, nerves regulating liver function accompany the hepatic artery and the portal vein, nerves regulating the stomach accompany the gastroduodenal arteries, nerves from the superior mesenteric plexus accompany the superior mesenteric artery and branch to the pancreas, small intestine and large intestine, and nerves of the inferior mesenteric plexus accompany the inferior mesenteric artery and branch to the large intestine, colon and rectum. These examples illustrate other organs that can be characterized and regulated using probes and techniques such as those described herein.

In treating kidney function, it is significant that renal sympathetic nerves have been identified as a major contributor to the complex pathophysiology of hypertension. Patients with hypertension generally have increased sympathetic drive to the kidneys, as evidenced by elevated rates of the renal norepinephrine "spillover." It is therefore believed that ablating renal sympathetic nerve function with sufficient energy will cause a reduction in both systolic and diastolic blood pressure, relieving hypertension in the patient.

Studies have shown that most nerves surrounding the renal arteries are within two millimeters of the renal artery, with nerves clustered more closely around the artery near the kidney, making measurement and treatment of the nerves from the renal artery practical. But, as complete destruction or ablation of the nerves is likely not desirable, monitoring nerve activity during or between nerve ablations, such as via the probes described herein, is an important tool in characterizing and regulating the degree to which nerve activity has been reduced. Before introduction of probes such as those described here, clinicians were unable to readily determine extent of renal sympathetic nerve modification during a procedure in a clinically relevant time frame, and could not measure durability of nerve damage during follow-up period after denervation. Now, with probes such as those described herein available, a clinician can take such measurements, and can to asses health of renal sympathetic nerves pre-procedurally to select or screen patients for denervation.

In operation, a clinician can measure nerve activity such as renal sympathetic nerve activity (RSNA) by emitting an electrical pulse through stimulation electrodes in the probe, and recording propagation along renal sympathetic nerve fibers using the sense electrode or electrodes on the probe. The clinician can then compare RSNA pre- and post-denervation to determine the degree of nerve ablation incurred, thereby more accurately achieving the desired degree of nerve ablation during treatment of the patient More specifically, a clinician can apply an electrical stimulus to a site in the proximal renal artery, and then monitor or record the nerve activity between the stimulus site and the kidney, thereby measuring the resultant downstream action potential in the nerve. Nerve ablation is then performed, and the stimulus and measurement of the nerve is repeated to verify a reduced or eliminated evoked potential detected in the nerve as a result of stimulation via the probe's electrodes.

The probe examples described in the examples here can therefore provide real-time feedback on functionality of renal sympathetic nerves, providing integrated evaluation of all nerve fibers surrounding a renal artery, at the artery proximal, distal, and renal branch locations. The probe is easily deployed via catheter-based delivery, and can be used as a standalone product or integrated with an ablation element. The probe system's low hardware and software costs and easy learning curve for clinical users make the probe system well-adapted for widespread adoption for treatment of nerve conditions such as those described herein.

A variety of experiments have been conducted to verify operation of probes such as those described herein, including using an isolated canine/porcine kidney and the associated vasculature to conduct certain tests. In one such test, probes such as those of FIGS. 1-6 were used to verify renal nerve health by measuring spontaneous renal sympathetic nerve activity (RSNA) using intraluminal microneurography, demonstrating that such probes cause effective stimulation and recording of RSNA. In the tests, stimulus-elicited response established a baseline recording of RSNA, and the circumferential section of renal nerve fibers were damaged using a scalpel. Remeasuring the stimulus-elicited response and comparing the response to the established baseline recording of RSNA confirmed that spontaneous sympathetic renal nerve activity had been reduced.

Figure 7:
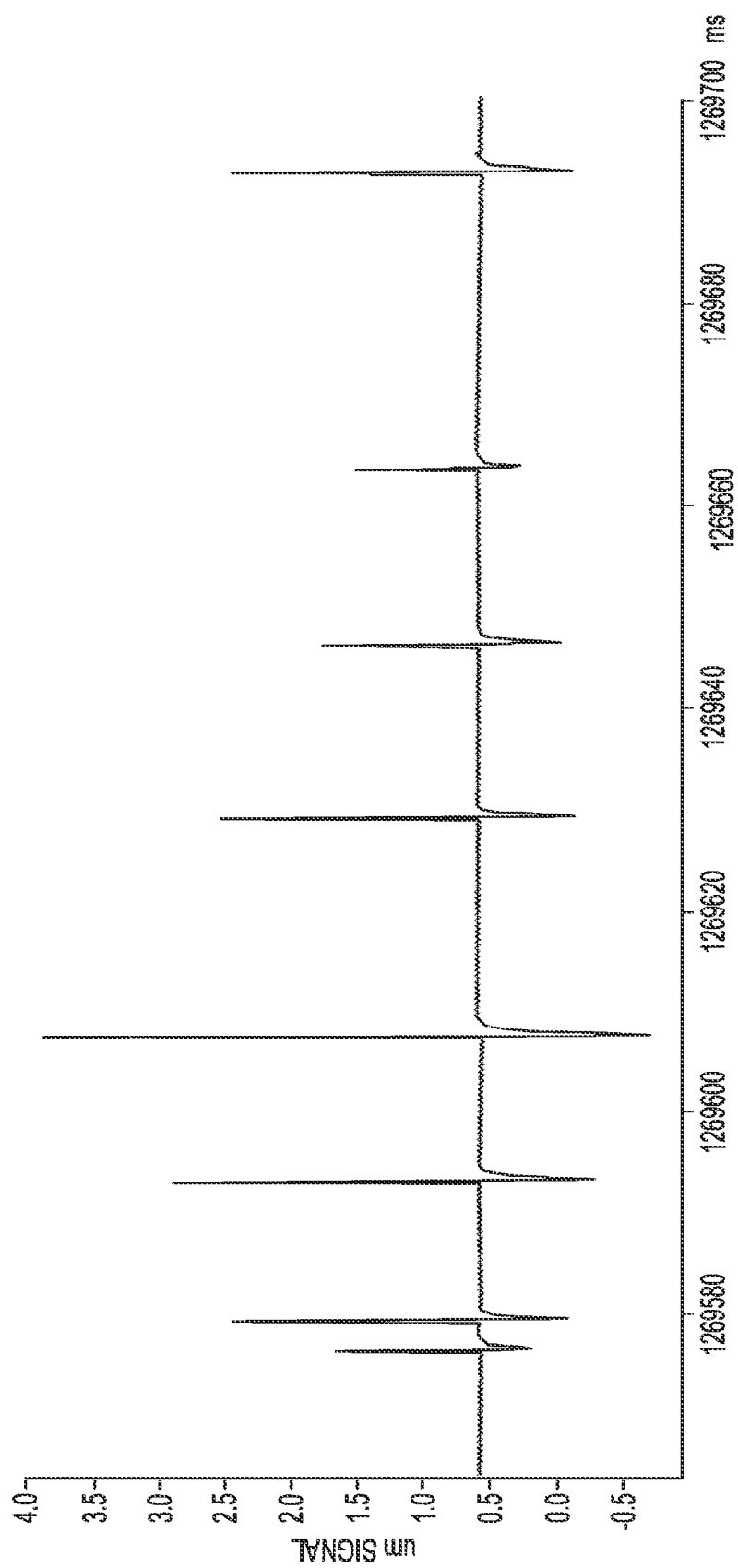
FIG. 7 shows spontaneous nerve activity, measured from the wall of the renal artery of an explanted kidney, consistent with an example.

FIG. 7 shows spontaneous nerve activity, measured from the wall of the renal artery of an explanted kidney. Here, the measurements are taken using needles placed in the wall of the renal artery, using relatively invasive microneurography techniques.

Figure 8:
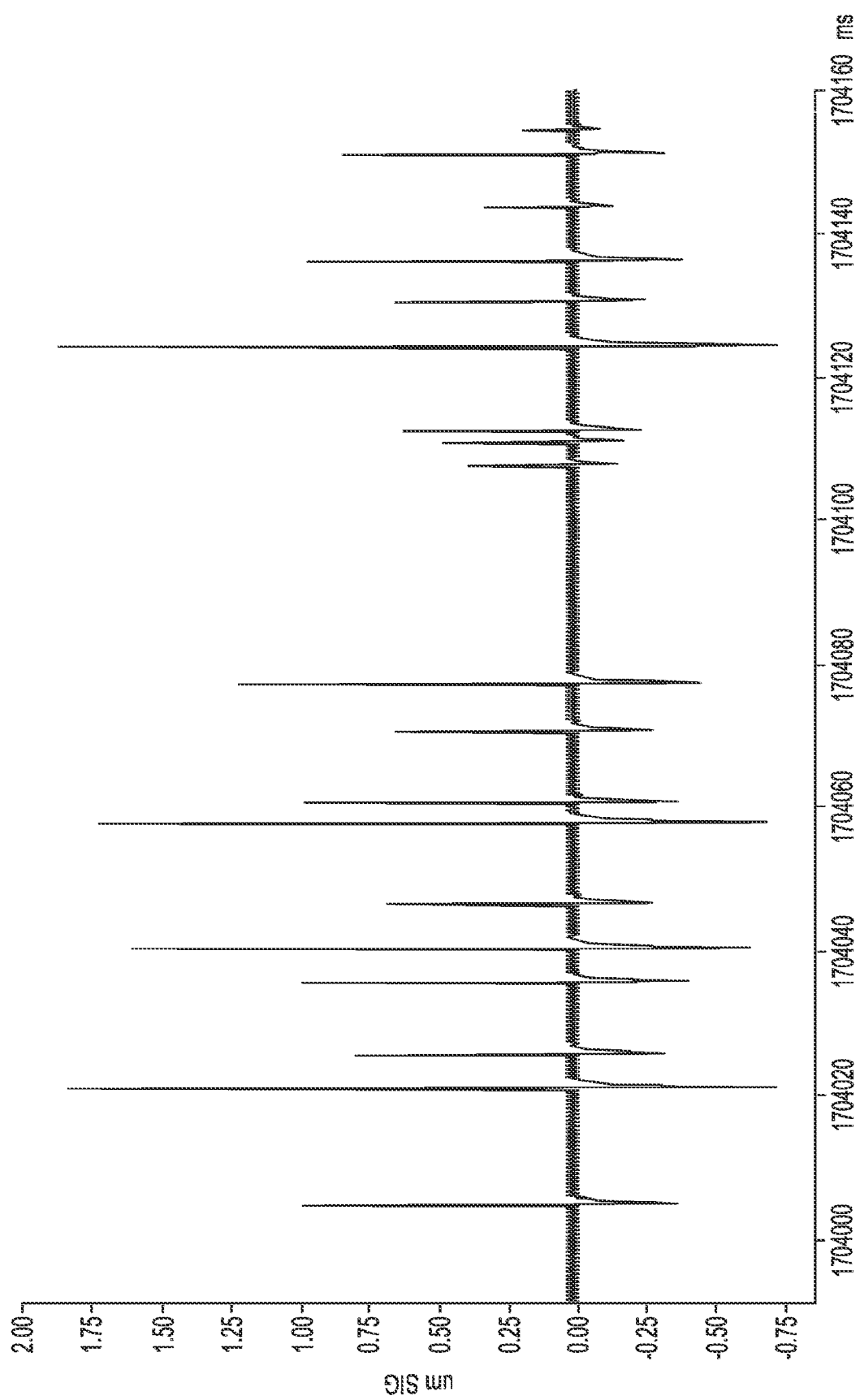
FIG. 8 shows spontaneous nerve activity in the wall of the renal artery of an explanted kidney using an intraluminal microneurography probe, consistent with an example.

FIG. 8 shows spontaneous nerve activity in the wall of the renal artery of an explanted kidney, using an intraluminal microneurography probe. Here, the peak signal levels me somewhat reduced relative to the method of FIG. 5, but accurate detection, measurement, and recording of spontaneous RSNA signals is shown to be achieved.

Figure 9:
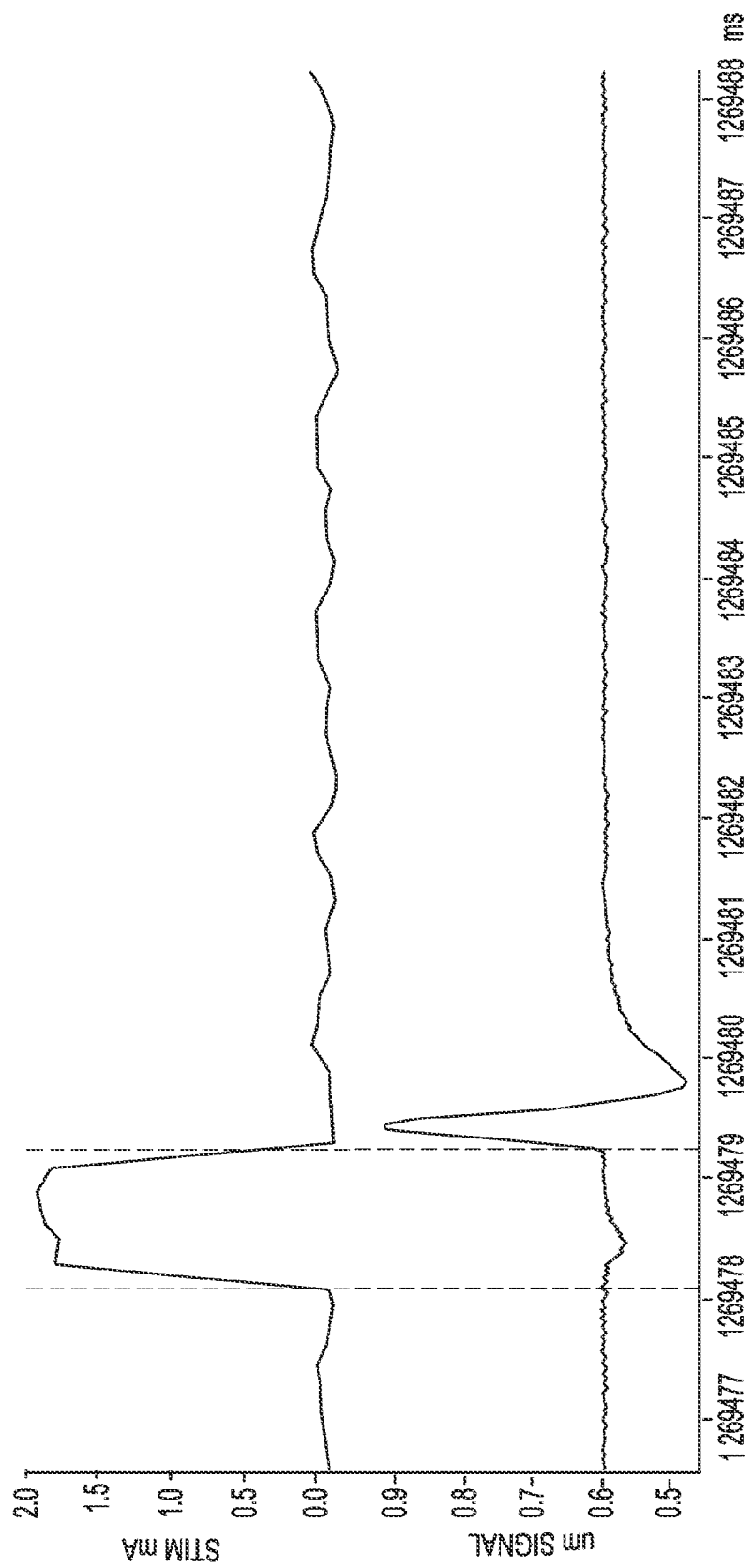
FIG. 9 shows a stimulus signal and the resulting measured RSNA action potential, consistent with an example.

In FIG. 9, a stimulus signal (top) and the resulting measured RSNA action potential are shown. Here, the renal nerve RSNA action potential is measured using needles in the artery wall, using a stimulus time of approximately 1.3 milliseconds, configured to avoid overlapping the stimulus and response signals based on the expected conduction velocity and the selected stimulus and sense electrode spacing.

Subsequent testing on live animals also proved successful, with a series of experiments conducted in a live rat model to confirm detection of renal sympathetic nerve activity (RSNA) in a living animal with competing signals from cardiac electrical activity and respiratory movement. Excellent results were achieve using probes having configurations such as those described herein, based on an experimental procedure in which an evoked RSNA baseline was determined in the intact renal artery, and RSNA was measured as the renal artery was transected.

Figure 10:
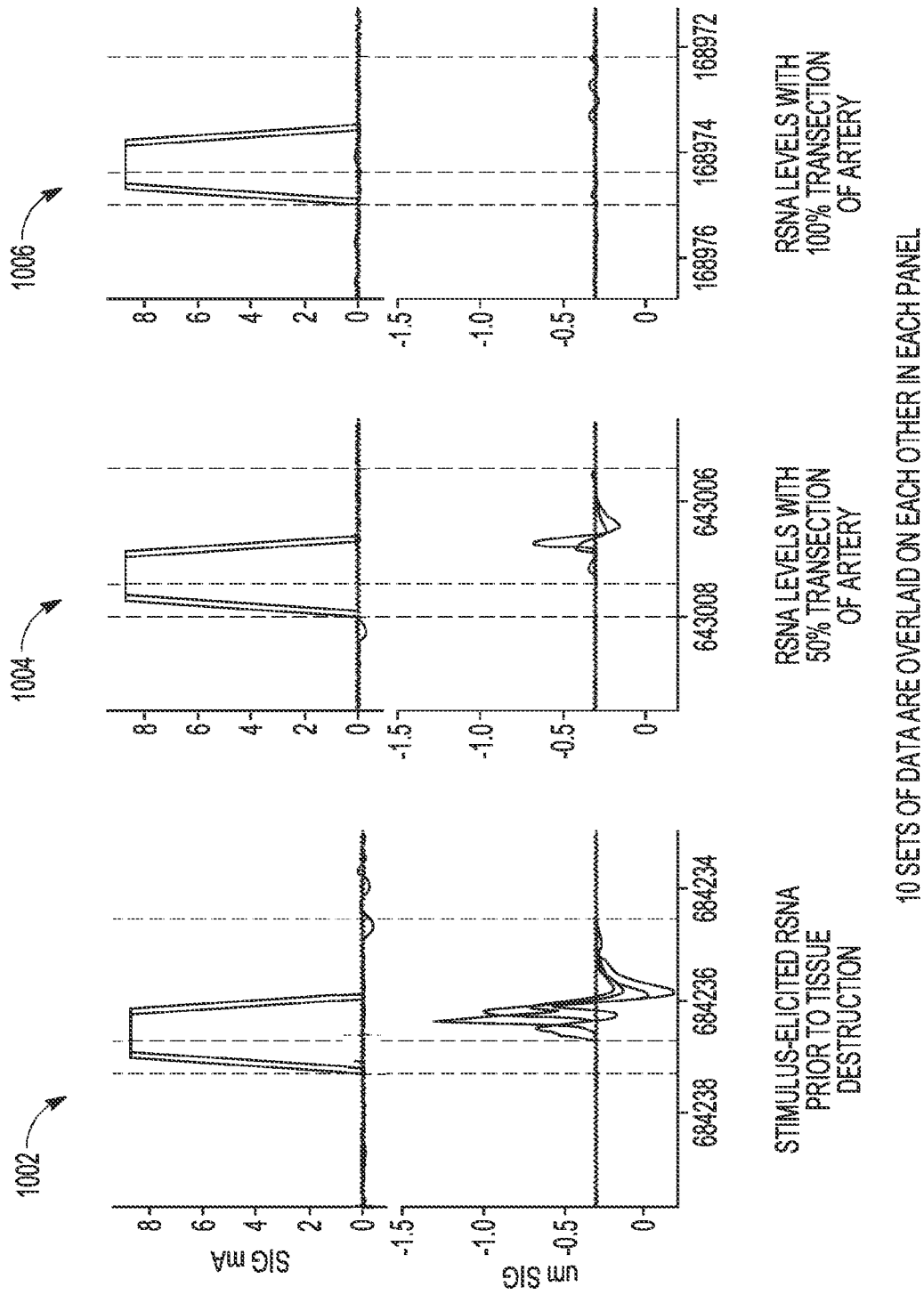
FIG. 10 shows destruction of the renal sympathetic nerves and the resulting effects on RSNA signals measured as a result of an applied stimulus signal, consistent with an example.

Destruction of the renal sympathetic nerves, and the resulting effects on RSNA signals measured as a result of an applied stimulus signal, are shown in FIG. 10. Here, ten sets of data are overlaid to generate a graph representative of typical levels and distribution of RSNA response to a stimulus signal as varying degrees of arterial transection. At 1002, the evoked RSNA baseline measurements taken prior to cutting across the artery are taken as a reference. At 1004, the artery is 50% transected, resulting in significant reduction in observed RSNA response, and at 1006, the artery is 100% transected, and little to no RSNA response is observed. In this example, transection of the renal arteries was used to destroy renal neural pathways because rat renal arteries are too small for effective radio frequency ablation.

Figure 11:
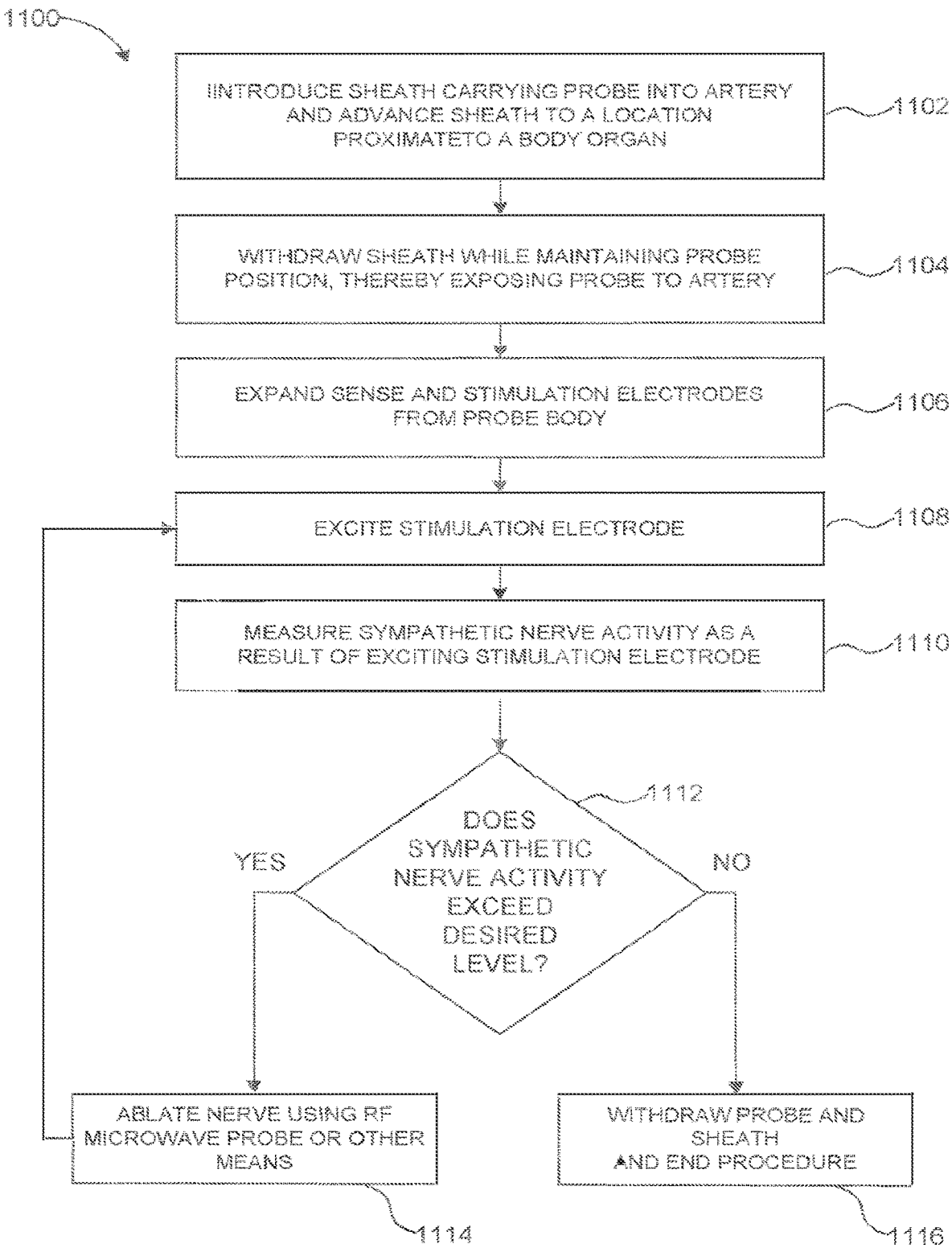
FIG. 11 is a flowchart illustrating a method of using an intraluminal microneurography probe to treat a medical condition, consistent with an example.

FIG. 11 is a flowchart illustrating a method of using an intraluminal microneurography probe to treat a medical condition, consistent with an example. As shown generally at 1100, a method of treating a medical condition involves using probe to excite and measure nerve activity near an organ, and selectively ablating nerve tissue near the probe until the desired nerve activity in response to the excitation is observed.

A sheath carrying the probe into the artery is inserted at 1102, and is advanced to a location in the artery near a body organ that is the subject of the medical condition and treatment, such as treating a kidney's neural sympathetic response to treat hypertension. The sheath is withdrawn slightly at 1104, exposing at least part of the probe including an expandable sense electrode and an expandable stimulation electrode to the artery. At 1106, the expandable stimulation and sense electrodes are expanded, such that the electrodes contact the arterial wall while permitting blood flow around the probe and the electrodes. At this point, the probe is properly deployed and ready to perform measurement.

The expandable stimulation electrode is excited at 1108, inducing an electrical signal into the nerves adjacent to the arterial wall. The nerves propagate the signal from the stimulation electrode, which can be observed at 1110 as sympathetic nerve activity as a result of exciting the stimulation electrode. The observed sympathetic nerve activity can then be measured, characterized, stored, viewed, etc., to determine whether the sympathetic nerve activity exceeds a desired level at 1112. If a desired level of sympathetic nerve activity is exceeded, nerves proximate the probe are ablated at 1114, such as using an radio frequency or microwave ablation element comprising a part of the probe located between the sense electrode and the stimulation electrode, as shown in FIGS. 5 and 6. Steps 1108-1112 are then repeated and the nerve is optionally ablated again, until the sympathetic nerve activity is determined not to exceed the desired level at 1112. At that point, the measurement and nerve ablation is complete, and the probe and sheath can be withdrawn at 1116.

Although the examples presented here primarily illustrate measurement of sympathetic nerve activity using the probe systems described, probe system such as those illustrated here can also be used to monitor organ activity, pain, or other nervous system indicia. For example, pain can be monitored during surgery in some applications, or nerve activity can be measured while externally stimulating an organ.

Although specific embodiments have been illustrated and described herein, any arrangement that achieve the same purpose, structure, or function may be substituted for the specific embodiments shown. This application is intended to cover any adaptations or variations of the example embodiments of the invention described herein. These and other embodiments are within the scope of the following claims and their equivalents.

What is claimed is:

1. An intraluminal microneurography probe, comprising:
a probe body configured to be introduced into a blood vessel near an organ of a body; and
an expandable sense electrode configured to expand from the probe body toward a wall of the blood vessel when introduced, wherein the expandable sense electrode comprises a continuously electrically exposed helical wire or mesh of wires that when expanded provide a continuous conductive outer circumference to permit an entire outer circumference of the expandable sense electrode to provide circumferential electrical contact with the wall of the blood vessel; and
an expandable stimulation electrode configured to expand from the probe body toward the wall of the blood vessel when introduced, wherein the expandable stimulation electrode comprises a continuously electrically exposed helical wire or mesh of wires that when expanded provide a continuous conductive outer circumference to permit an entire outer circumference of the expandable stimulation electrode to provide circumferential electrical contact with the wall of the blood vessel;
wherein the expandable sense electrode and the expandable stimulation electrode are spaced a distance apart sufficient to enable the expandable sense electrode to be used to accurately detect a typical nerve action potential without interference from the expandable stimulation electrode.

2. The intraluminal microneurography probe of claim 1, wherein the distance apart, which the expandable sense electrode and the expandable stimulation electrode are spaced, is substantially 3 centimeters.

3. The intraluminal microneurography probe of claim 2, wherein a diameter of the probe body is 2.5 millimeters or less.

4. The intraluminal microneurography probe of claim 2, further comprising a neural ablation element attached to the probe body.

5. The intraluminal microneurography probe of claim 4, wherein the neural ablation element is attached to the probe body at a location between the expandable sense electrode and the expandable stimulation electrode.

6. The intraluminal microneurography probe of claim 4, wherein the neural ablation element comprises a radio frequency ablation element or a microwave frequency ablation element.

7. The intraluminal microneurography probe of claim 4, further comprising a liquid cooling element configured to cool the neural ablation element.

8. The intraluminal microneurography probe of claim 1, wherein:
   the expandable sense electrode is fixed to the probe body at a first end of the expandable sense electrode and is movable relative to the probe body at a second end of the expandable sense electrode such that movement of the second end of the expandable sense electrode towards the first end of the expandable sense electrode causes the expandable sense electrode to expand; and
   the expandable stimulation electrode is fixed to the probe body at a first end of the expandable stimulation electrode and is movable relative to the probe body at a second end of the expandable stimulation electrode such that movement of the second end of the expandable stimulation electrode towards the first end of the expandable stimulation electrode causes the expandable sense electrode to expand.

9. The intraluminal microneurography probe of claim 8, further comprising:
   a first slidable collar to which the second end of the expandable sense electrode is connected; and
   a second slidable collar to which the second end of the expandable stimulation electrode is connected;
   movement of the first slidable collar transitions the expandable sense electrode between a collapsed position and an expanded position of the expandable sense electrode; and
   movement of the second slidable collar transitions the expandable stimulation electrode between a collapsed position and an expanded position of the expandable sense electrode.

10. The intraluminal microneurography probe of claim 1, wherein:
    each of the expandable sense electrode and the expandable stimulation electrode is configured to transition between a collapsed position and an expanded position;
    the helical wire or mesh of wires of the expandable sense electrode are closely wrapped around the probe body when the expandable sense electrode is in the collapsed position, and extend away from the probe body when the expandable sense electrode is in the expanded position; and
    the helical wire or mesh of wires of the expandable stimulation electrode are closely wrapped around the probe body when the expandable stimulation electrode is in the collapsed position, and extend away from the probe body when the expandable stimulation electrode is in the expanded position.

11. The intraluminal microneurography probe of claim 1, wherein the expandable stimulation electrode is substantially larger than the expandable sense electrode to avoid hyperpolarization of a nerve during stimulation thereof.

12. An intraluminal microneurography system, comprising:
    a stimulation circuit;
    a sense circuit; and
    an intraluminal microneurography probe including a probe body, an expandable sense electrode electrically coupled to the sense circuit, and an expandable stimulation electrode electrically coupled to the stimulation circuit;
    the probe body of the intraluminal microneurography probe configured to be introduced into a blood vessel near an organ of a body; and
    the expandable sense electrode of the intraluminal microneurography probe configured to expand from the probe body toward a wall of the blood vessel when introduced, wherein the expandable sense electrode comprises a continuously electrically exposed helical wire or mesh of wires that when expanded provide a continuous conductive outer circumference to permit an entire outer circumference of the expandable sense electrode to provide circumferential electrical contact with the wall of the blood vessel;
    the expandable stimulation electrode of the intraluminal microneurography probe configured to expand from the probe body toward the wall of the blood vessel when introduced, wherein the expandable stimulation electrode comprises a continuously electrically exposed helical wire or mesh of wires that when expanded provide a continuous conductive outer circumference to permit an entire outer circumference of the expandable stimulation electrode to provide circumferential electrical contact with the wall of the blood vessel; and
    the expandable sense electrode and the expandable stimulation electrode of the intraluminal microneurography probe are spaced a distance apart sufficient to enable the expandable sense electrode to be used to accurately detect a typical nerve action potential without interference from the expandable stimulation electrode.

13. The intraluminal microneurography system of claim 12, wherein the stimulation circuit is configured to provide one or more stimulation pulses to the expandable stimulation electrode of the intraluminal microneurography probe.

14. The intraluminal microneurography system of claim 12, wherein the sense circuit is configured to sense neural activity of one or more nerves adjacent to the blood vessel.

15. The intraluminal microneurography system of claim 12, further comprising:
    first and second ground electrodes;
    wherein the stimulation circuit is electrically coupled to the expandable stimulation electrode and the first ground electrode; and
    wherein the sense circuit is electrically coupled to the expandable sense electrode and the second ground electrode.

16. The intraluminal microneurography system of claim 15, further comprising a filter electrically coupled between the first and the second ground electrodes.

17. The intraluminal microneurography system of claim 16, wherein the filter comprises a low-pass filter.

18. The intraluminal microneurography system of claim 14, further comprising a neural ablation element attached to the probe body of the intraluminal microneurography probe.

19. The intraluminal microneurography system of claim 18, wherein the neural ablation element is attached to the probe body at a location between the expandable sense electrode and the expandable stimulation electrode.

20. The intraluminal microneurography system of claim 18, wherein the neural ablation element comprises a radio frequency ablation element or a microwave frequency ablation element.

* * * * *